US009877854B2

United States Patent
Rao et al.

(10) Patent No.: US 9,877,854 B2
(45) Date of Patent: Jan. 30, 2018

(54) STENT DELIVERY SYSTEM

(71) Applicant: Boston Scientific Scimed, Inc., Maple Grove, MN (US)

(72) Inventors: Doreen Rao, Sudbury, MA (US); Ronald Ciulla, Westford, MA (US); Joshin Sahadevan, Bangalore (IN); Debasish Sarangi, Bangalore (IN); Rahul Mishra, Bangalore (IN)

(73) Assignee: Boston Scientific Scimed, Inc., Maple Grove, MN (US)

( * ) Notice: Subject to any disclaimer, the term of this patent is extended or adjusted under 35 U.S.C. 154(b) by 221 days.

(21) Appl. No.: 14/707,221

(22) Filed: May 8, 2015

(65) Prior Publication Data
US 2015/0335452 A1     Nov. 26, 2015

Related U.S. Application Data

(60) Provisional application No. 62/001,300, filed on May 21, 2014.

(51) Int. Cl.
| | | |
|---|---|---|
| *A61F 2/95* | (2013.01) | |
| *A61F 2/82* | (2013.01) | |
| *A61F 2/966* | (2013.01) | |
| *A61F 2/04* | (2013.01) | |

(52) U.S. Cl.
CPC .............. *A61F 2/95* (2013.01); *A61F 2/82* (2013.01); *A61F 2/966* (2013.01); *A61F 2002/048* (2013.01); *A61F 2002/9517* (2013.01)

(58) Field of Classification Search
CPC .. A61F 2/95; A61F 2/966; A61F 2/962; A61F 2002/9517
See application file for complete search history.

(56) References Cited

U.S. PATENT DOCUMENTS

| | | | |
|---|---|---|---|
| 4,610,657 | A | 9/1986 | Densow |
| 4,713,049 | A | 12/1987 | Carter |
| 4,787,884 | A | 11/1988 | Goldberg |
| 4,957,479 | A | 9/1990 | Roemer |
| 4,986,814 | A | 1/1991 | Burney et al. |
| 5,052,998 | A | 10/1991 | Zimmon |
| 5,116,309 | A | 5/1992 | Coll |

(Continued)

FOREIGN PATENT DOCUMENTS

| | | |
|---|---|---|
| EP | 1041949 A1 | 10/2000 |
| EP | 1251796 B1 | 12/2004 |

(Continued)

*Primary Examiner* — Katrina Stransky

(57) ABSTRACT

A stent delivery device having a locking mechanism. The device includes a handle assembly, an elongate inner member, and an elongate outer tubular member surrounding the elongate inner member. The handle assembly includes a handle attached to one of the inner member and the outer tubular member, and an actuator attached to the other of the inner member and the outer tubular member. Actuation of the actuator relative to the handle between a first position and a second position causes axial movement of the outer tubular member relative to the inner member. The locking mechanism has a locked position in which the actuator is prevented from moving from the first position to the second position and an unlocked position in which the actuator is permitted to move from the first position to the second position.

18 Claims, 22 Drawing Sheets

(56) References Cited

U.S. PATENT DOCUMENTS

| | | |
|---|---|---|
| 5,152,749 A | 10/1992 | Giesy et al. |
| 5,221,253 A | 6/1993 | Coll |
| 5,295,954 A | 3/1994 | Sachse |
| 5,334,185 A | 8/1994 | Giesy et al. |
| 5,346,467 A | 9/1994 | Coll |
| 5,364,340 A | 11/1994 | Coll |
| 5,407,435 A | 4/1995 | Sachse |
| 5,409,468 A | 4/1995 | Sachse |
| 5,433,723 A | 7/1995 | Lindenberg et al. |
| 5,484,444 A | 1/1996 | Braunschweiler et al. |
| 5,573,530 A | 11/1996 | Fleury et al. |
| 5,707,376 A | 1/1998 | Kavteladze et al. |
| 5,776,142 A | 7/1998 | Gunderson |
| 5,782,855 A | 7/1998 | Lau et al. |
| 5,843,091 A | 12/1998 | Holsinger et al. |
| 5,921,952 A | 7/1999 | Desmond, III et al. |
| 6,117,141 A | 9/2000 | Ouchi |
| 6,190,360 B1 | 2/2001 | Iancea et al. |
| 6,248,100 B1 | 6/2001 | de Toledo et al. |
| 6,258,101 B1 | 7/2001 | Blake, III |
| 6,395,017 B1 | 5/2002 | Dwyer et al. |
| 6,514,261 B1 | 2/2003 | Randall et al. |
| 6,572,643 B1 | 6/2003 | Gharibadeh |
| 6,629,981 B2 | 10/2003 | Bui et al. |
| 6,685,734 B1 | 2/2004 | Vaelimaa et al. |
| 6,749,627 B2 | 6/2004 | Thompson et al. |
| 6,786,918 B1 | 9/2004 | Krivoruchko et al. |
| 6,866,669 B2 | 3/2005 | Buzzard et al. |
| 6,939,352 B2 | 9/2005 | Buzzard et al. |
| 7,105,016 B2 | 9/2006 | Shiu et al. |
| 7,122,050 B2 | 10/2006 | Randall et al. |
| 7,381,216 B2 | 6/2008 | Buzzard et al. |
| 7,419,501 B2 | 9/2008 | Chiu et al. |
| 7,476,244 B2 | 1/2009 | Buzzard et al. |
| 7,550,012 B2 | 6/2009 | Lavelle |
| 7,566,342 B2 | 7/2009 | Parker et al. |
| 7,608,099 B2 | 10/2009 | Johnson et al. |
| 7,766,952 B2 | 8/2010 | Horan et al. |
| 7,837,724 B2 | 11/2010 | Keeble et al. |
| 7,967,829 B2 | 6/2011 | Gunderson et al. |
| 8,216,296 B2 | 7/2012 | Wu et al. |
| 8,257,420 B2 | 9/2012 | Fitzgerald et al. |
| 8,267,987 B2 | 9/2012 | Johnson et al. |
| 8,382,813 B2 | 2/2013 | Shumer |
| 8,475,514 B2 | 7/2013 | Hartley et al. |
| 2005/0080476 A1 | 4/2005 | Gunderson et al. |
| 2009/0192518 A1* | 7/2009 | Golden ............... A61F 2/95 606/108 |
| 2011/0295265 A1 | 12/2011 | Hollett et al. |
| 2011/0313404 A1 | 12/2011 | Amos et al. |
| 2012/0310320 A1 | 12/2012 | Gill et al. |
| 2013/0297011 A1* | 11/2013 | Morris ............... A61F 2/2436 623/2.11 |

FOREIGN PATENT DOCUMENTS

| | | |
|---|---|---|
| EP | 1251797 B1 | 11/2007 |
| EP | 1482870 B1 | 8/2010 |
| EP | 2089089 B1 | 8/2010 |

* cited by examiner

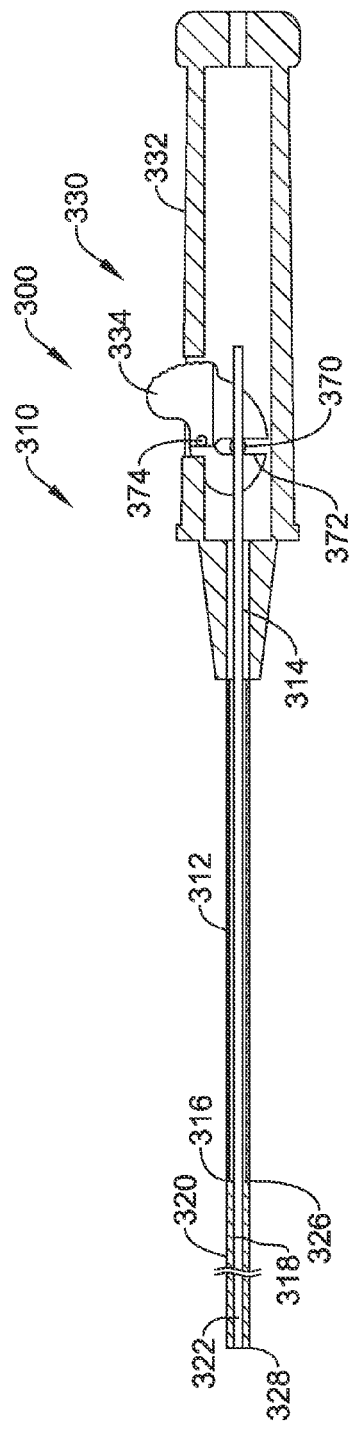
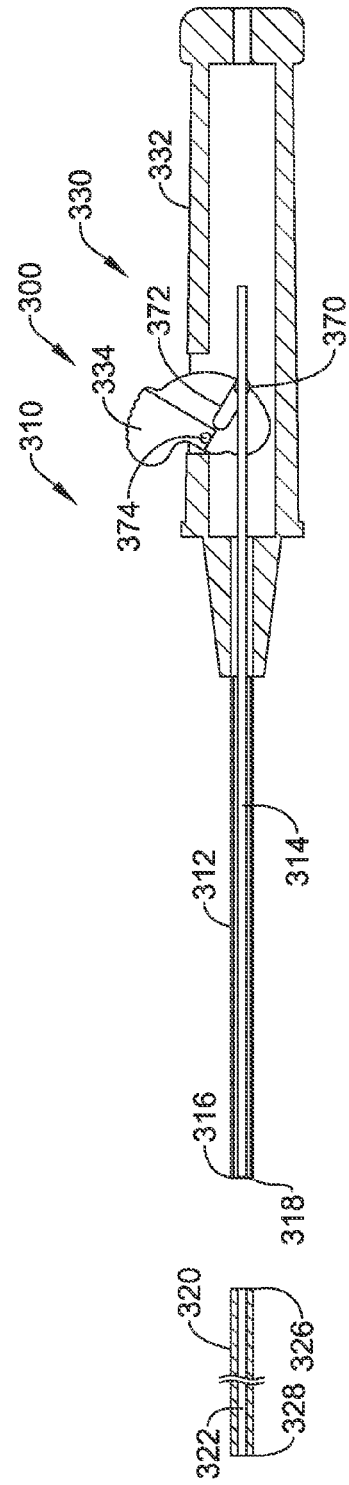
FIG. 11A
FIG. 11B

STENT DELIVERY SYSTEM

CROSS-REFERENCE TO RELATED APPLICATIONS

This application claims priority under 35 U.S.C. § 119(e) to U.S. Provisional Application No. 62/001,300, filed May 21, 2014, the entire disclosure of which is herein incorporated by reference.

TECHNICAL FIELD

The disclosure is directed to stent delivery systems for deploying a stent in a body lumen. More particularly, the disclosure is directed to stent delivery systems for delivering a ureteral stent to a ureter and deploying the stent in the ureter of a patient.

BACKGROUND

Stents have been used to establish and/or maintain open pathways through body lumens, such as the trachea, arteries, blood vessels, as well as urinary, biliary, esophageal or renal tracts, etc. For example, a ureteral stent may be placed in the ureter to maintain an open pathway for fluid between the kidney and the bladder.

In some instances, a guidewire may be advanced through the body lumen, such as the ureter of a patient, and then a stent delivery device, having a stent mounted thereon may be advanced over the guidewire to the desired location within the body lumen. The stent may then be deployed from the stent delivery device, and the stent delivery device may be withdrawn from the body lumen, leaving the stent positioned in the body lumen.

Accordingly, it may be desirable to provide alternative stent delivery devices which enable the user to steer, rotate, push, pull or otherwise manipulate a stent, such as a ureteral stent, during the placement process to ensure proper positioning. Additionally or alternatively, it may also be desirable to provide alternative deployment mechanisms which may include locking mechanisms to prevent premature deployment of the stent.

SUMMARY

The disclosure is directed to several alternative designs, materials and methods of manufacturing medical device structures and assemblies, and uses thereof.

Accordingly, one illustrative embodiment is a stent delivery device. The stent delivery device includes a handle assembly, an elongate inner member extending distally from the handle assembly along a longitudinal axis, and an elongate outer tubular member extending distally from the handle assembly along the longitudinal axis about the elongate inner member. The handle assembly includes a handle attached to one of the inner member and the outer tubular member, and an actuator attached to the other of the inner member and the outer tubular member. Actuation of the actuator relative to the handle between a first position and a second position causes axial movement of the outer tubular member relative to the inner member. The handle assembly also includes a locking mechanism for restricting actuation of the actuator from the first position to the second position. The locking mechanism has a locked position and an unlocked position. In the locked position the actuator is prevented from moving from the first position to the second position and in the unlocked position the actuator is permitted to move from the first position to the second position.

Another illustrative embodiment is a stent delivery assembly. The stent delivery assembly includes a handle assembly, an elongate outer tubular member extending distally from the handle assembly along a longitudinal axis, and an elongate inner member extending distally from the handle assembly through the lumen of the outer tubular member. A distal portion of the elongate inner member extends distal of the distal end of the outer tubular member. The assembly also includes a tubular stent disposed about the distal portion of the inner member. The handle assembly includes a handle attached to one of the inner member and the outer tubular member, and an actuator attached to the other of the inner member and the outer tubular member. Actuation of the actuator relative to the handle from a first position to a second position causes axial movement of the outer tubular member relative to the inner member to deploy the stent from the distal portion of the inner member. The handle assembly also includes a locking mechanism for restricting actuation of the actuator from the first position to the second position to prevent premature deployment of the stent. The locking mechanism has a locked position and an unlocked position. In the locked position the actuator is prevented from moving from the first position to the second position and in the unlocked position the actuator is permitted to move from the first position to the second position to deploy the stent.

Yet another illustrative embodiment is a method of manipulating a stent delivery device. The method includes grasping a handle of a handle assembly of the stent delivery device with a hand. The stent delivery device includes an elongate inner member extending distally from the handle assembly along a longitudinal axis, an elongate outer tubular member extending distally from the handle assembly along the longitudinal axis about the elongate inner member, an actuator movable relative to the handle for providing longitudinal movement of the outer tubular member relative to the inner tubular member, and a stent surrounding a distal end portion of the inner member. The method further includes moving a locking mechanism from a locked position to an unlocked position. In the locked position the locking mechanism prevents longitudinal movement of the outer tubular member relative to the inner tubular member and in the unlocked position longitudinal movement of the outer tubular member relative to the inner tubular member is permitted. The method further includes subsequent to moving the locking mechanism to the unlocked position, actuating the actuator from a first position to a second position to deploy the stent from the stent delivery device. In the locked position the actuator is prevented from moving from the first position to the second position and in the unlocked position the actuator is permitted to move from the first position to the second position.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which:

FIGS. 11A-11B are longitudinal cross-sectional views of another stent delivery system illustrating stent deployment in accordance with this disclosure;

Figure 1:
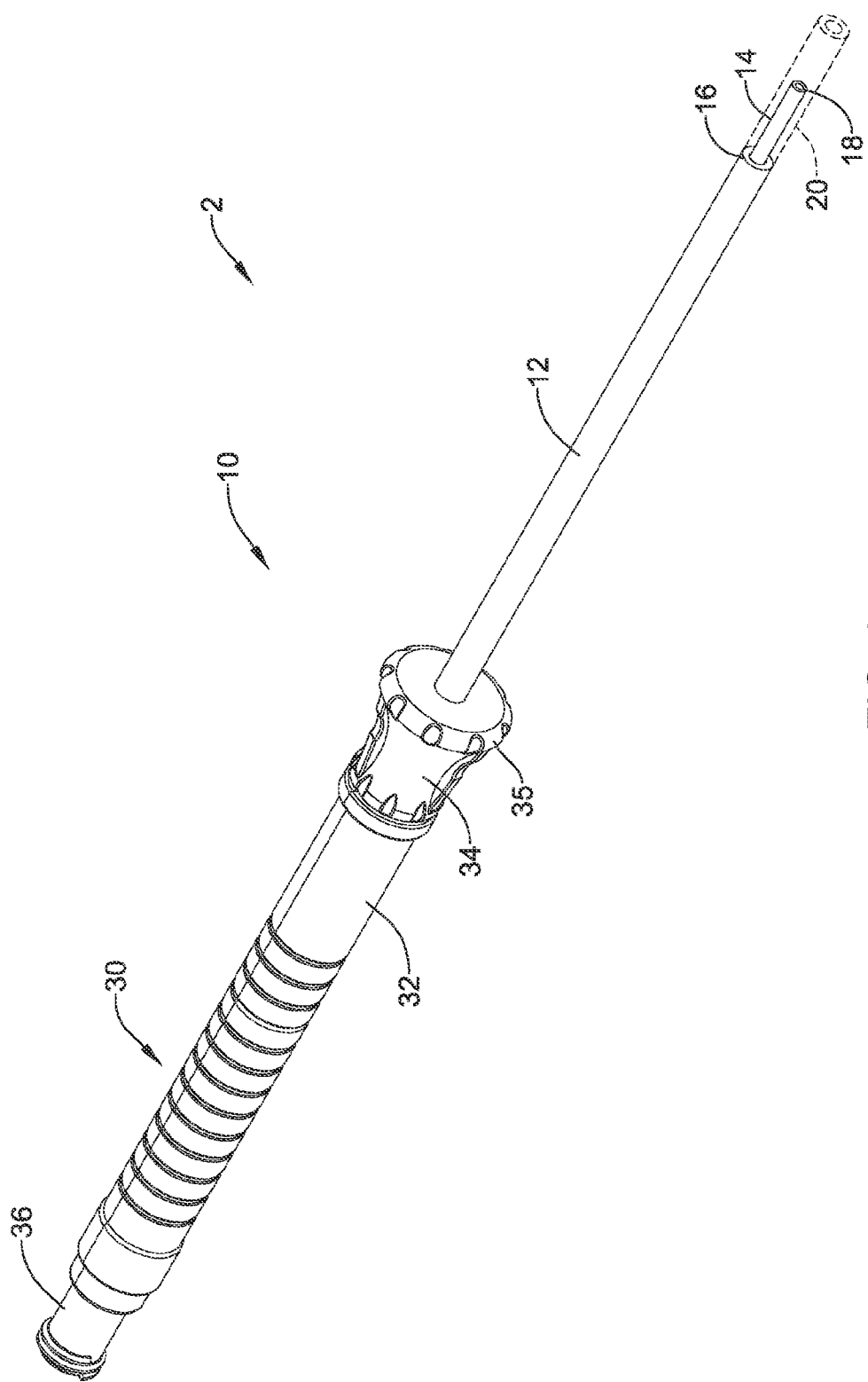
FIG. 1 is a perspective view of an exemplary stent delivery system in accordance with this disclosure.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

One illustrative stent delivery device includes a handle assembly, an elongate inner member extending distally from the handle assembly along a longitudinal axis, and an elongate outer tubular member extending distally from the handle assembly along the longitudinal axis about the elongate inner member. The outer tubular member has a proximal end and a distal end, and the inner member has a proximal end and a distal end.

The handle assembly may include a handle attached to one of the inner member and the outer tubular member, and an actuator attached to the other of the inner member and the outer tubular member. Actuation of the actuator relative to the handle between a first position and a second position causes axial movement of the outer tubular member relative to the inner member. Movement of the outer tubular member relative to the inner member may be achieved by rotational movement, linear movement, or a combination of rotational and linear movement of the actuator relative to the handle, for example. Some specific examples of actuators which may be used with the stent delivery device are further described herein.

In some instances, the handle assembly may also include a locking mechanism for restricting actuation of the actuator from the first position to the second position. Different locking mechanisms may be used with different actuators and actuation mechanisms. The locking mechanism may have a locked position and an unlocked position, wherein in the locked position the actuator is prevented from moving from the first position to the second position and in the unlocked position the actuator is permitted to move from the first position to the second position.

Figure 1A:
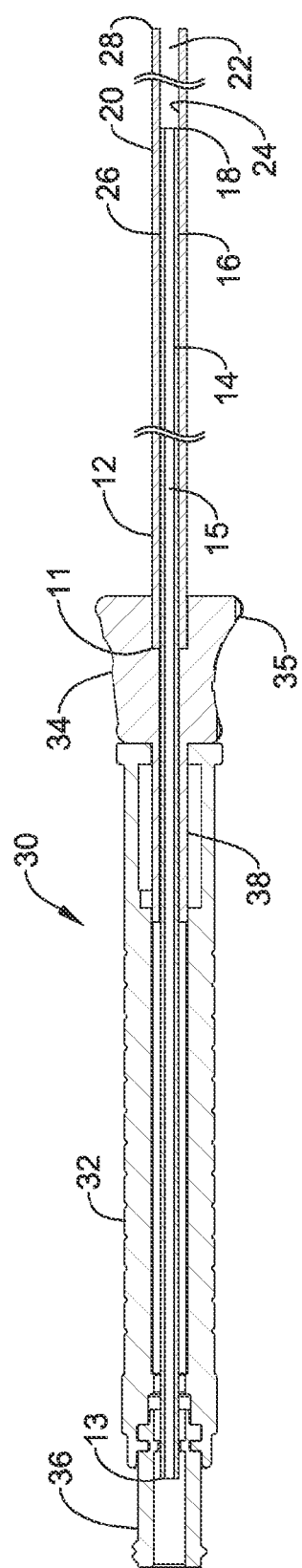
FIG. 1A is a longitudinal cross-sectional view of the stent delivery system of FIG. 1.

An exemplary stent delivery system 2 is illustrated in FIGS. 1 through 4A. The stent delivery system 2 may include a stent delivery device 10 configured to deliver a stent 20 (shown in phantom), such as a ureteral stent, to a body lumen. The stent delivery system 2 is shown in a first position in FIGS. 1 and 1A. The stent delivery device 10 may include an outer tubular member 12, an inner elongate member 14 extending through the lumen 17 of the outer tubular member 12, and a handle assembly 30.

The outer tubular member 12, which may have a proximal end 11 coupled to and/or positioned in the handle assembly 30, may extend distally from the handle assembly 30 along a longitudinal axis to a distal end 16 of the outer tubular member 12. Furthermore, the elongate inner member 14, which may have a proximal end 13 coupled to and/or positioned in the handle assembly 30, may extend distally from the handle assembly 30 along the longitudinal axis to a distal end 18 of the elongate inner member 14. In some instances, the elongate inner member 14 may be a tubular member having a lumen 15 extending therethrough from the proximal end 13 to the distal end 18 of the elongate inner member 14. The lumen 15 may be sized to accommodate a guidewire therethrough such that the stent delivery device 10 and associated stent 20 may be advanced through a body lumen over a guidewire.

The stent 20 may be disposed proximate the distal end of the stent delivery device 10 for delivery to a body lumen. The stent 20 may be a tubular stent having a proximal end 26, a distal end 28, and a lumen 22 extending therethrough from the proximal end 26 to the distal end 28. In some instances, the stent 20 may be positionable on and surround a distal end region of the elongate inner member 14 in the first position. The distal end region of the elongate inner member 14 may extend distal of the distal end 16 of the outer tubular member 12 in the first position, with the stent 20 positioned distal of the outer tubular member 12. For example, the proximal end 26 of the stent 20 may abut the distal end 16 of the outer tubular member 12 when the stent 20 is secured to the stent delivery device 10 in the first position. In some instances the outer diameter of the distal end region of the elongate inner member 14 may be sized slightly larger than the inner diameter of the stent 20 such that the distal end region of the elongate inner member 14 frictionally engages the inner surface 24 of the stent 20 to secure the stent 20 onto the distal end region of the elongate inner member 14. As discussed later herein, actuation of the outer tubular member 12 distally relative to the inner member 14 may overcome the frictional force to deploy the stent 20 from the inner member 14. In other embodiments, the stent 20 may be secured to the stent delivery device 10 in other ways. For example, in some instances, the stent 20 may surround a distal end region of the inner member 14 while positioned within the lumen of the outer tubular member 12. In such an embodiment, the stent 20 may be expelled from the distal end of the outer tubular member 12 via relative longitudinal movement of the inner and outer members to deploy the stent 20.

The handle assembly 30 may include a handle 32 to be grasped by a user and an actuator 34 movable by a user relative to the handle 32. The handle 32 may be attached, such as fixedly secured, to one of the inner member 14 and the outer tubular member 12, and the actuator 34 may be attached, such as fixedly secured, to the other of the inner member 14 and the outer tubular member 12. Accordingly, actuation of the actuator 34 relative to the handle 32 may correspondingly move the inner member 14 relative to the outer tubular member 12. For example, rotation of the actuator 34 about the longitudinal axis relative to the handle 23 may rotate the inner member 14 relative to the outer tubular member 12 and/or longitudinal movement of the actuator 34 along the longitudinal axis relative to the handle 32 may move the inner member 14 longitudinally relative to the outer tubular member 12. As discussed further herein, actuation of the actuator 34 relative to the handle 32 between the first position (FIG. 1) to a second position (FIG. 4) may cause axial movement of the outer tubular member 12 relative to the inner member 14 to deploy the stent 20 (e.g., move the inner member 14 proximally and/or move the outer member 12 distally). In the illustrated embodiment, the actuator 34 is fixedly secured to the outer tubular member 12 and the handle 32 is fixedly secured to the inner member 14. However, in other embodiments, the actuator 34 may be fixedly secured to the inner member 14 and the handle 32 may be fixedly secured to the outer tubular member 12, if desired.

The handle assembly 30 may also include a locking mechanism 50 for restricting actuation of the actuator 34 from the first position to the second position. For example, the locking mechanism 50 may have a locked position in which the actuator 34 is prevented from moving from the first position to the second position and an unlocked position in which the actuator 34 is permitted to move from the first position to the second position.

Figure 2:
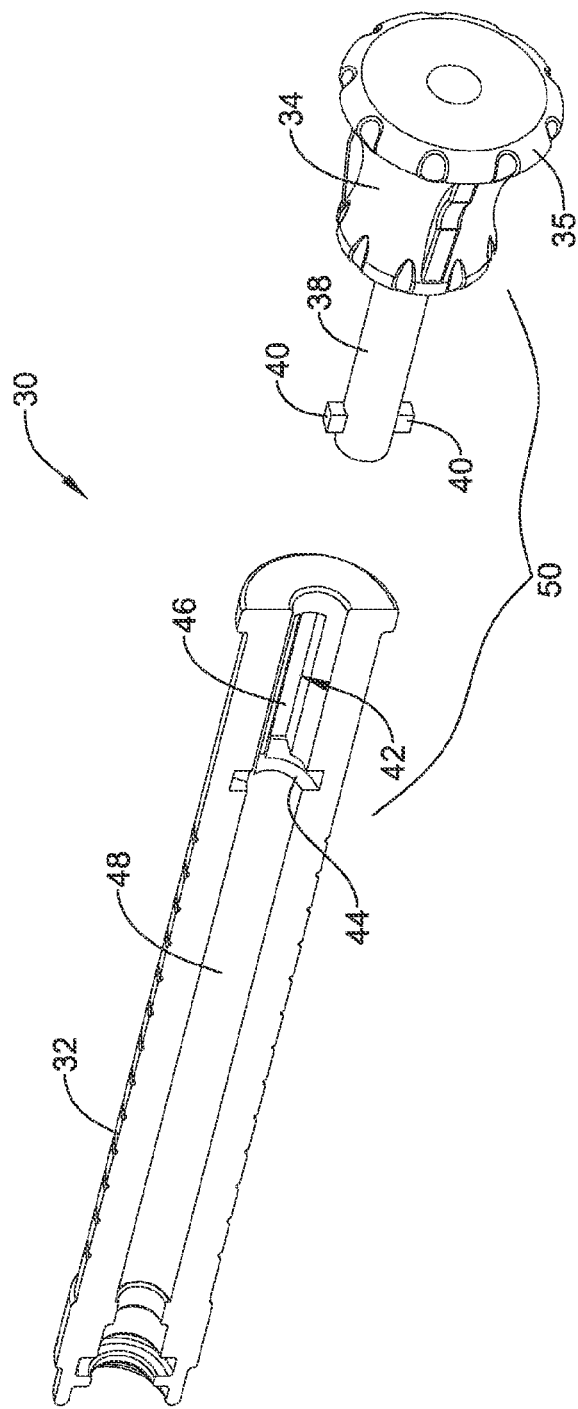
FIG. 2 is a perspective view of components of the stent delivery system of FIG. 1.

Features of the locking mechanism 50 are further illustrated in FIG. 2. As shown in FIG. 2, the actuator 34 may include a knob 35 and an extension 38 extending proximally from the knob 35. The knob 35 may be positioned distal of the handle 32 with the extension 38 extending proximally from the knob 35 into the bore 48 of the handle 32 when assembled with the handle 32. The extension 38 may include one or more features configured to mate with one or more features of the handle 32. For example, the extension 38 may include one or more protrusions 40, or a plurality of protrusions 40, extending radially outward from the extension 38. In the illustrated embodiment, the actuator 34 includes a pair of protrusions 40 extending radially outward from the extension 38 in opposite directions. The handle 32 may include one or more channels 42, or a plurality of channels 42 configured to receive the protrusion(s) 40 therein. In the illustrated embodiment, the handle 32 includes a pair of channels 42 (only one of which is shown in FIG. 2) positioned on opposite sides of the bore 48 through the handle 32. The channel(s) 42 may include a circumferential portion 44 extending circumferentially around the bore 48 of the handle 32 and a longitudinal portion 46 extending parallel to the longitudinal axis of the bore 48. The circumferential portion 44 may extend less than 360° in some instances. In the illustrated embodiment, the longitudinal portion 46 may extend distally from the circumferential portion 44 toward the distal end of the handle 32.

The locking mechanism 50 may be configured such that when the protrusion(s) 40 is/are disposed in the circumferential portion(s) 44 of the channel(s) 42 and not aligned with the longitudinal portion(s) 46 (i.e., in the locked position) the actuator 34 may be prevented from moving from the first position to the second position. When the protrusion(s) 40 is/are rotated in the channel(s) 42 into longitudinal alignment with the longitudinal portion(s) 46 (i.e., in the unlocked position) the actuator 34 may be permitted to move from the first position to the second position as the protrusion(s) move longitudinally in the longitudinal portion(s) 46 of the channel(s) 42. Thus, longitudinal movement of the outer tubular member 12 relative to the inner member 14 is precluded in the locked position and permitted in the unlocked position.

Figure 3:
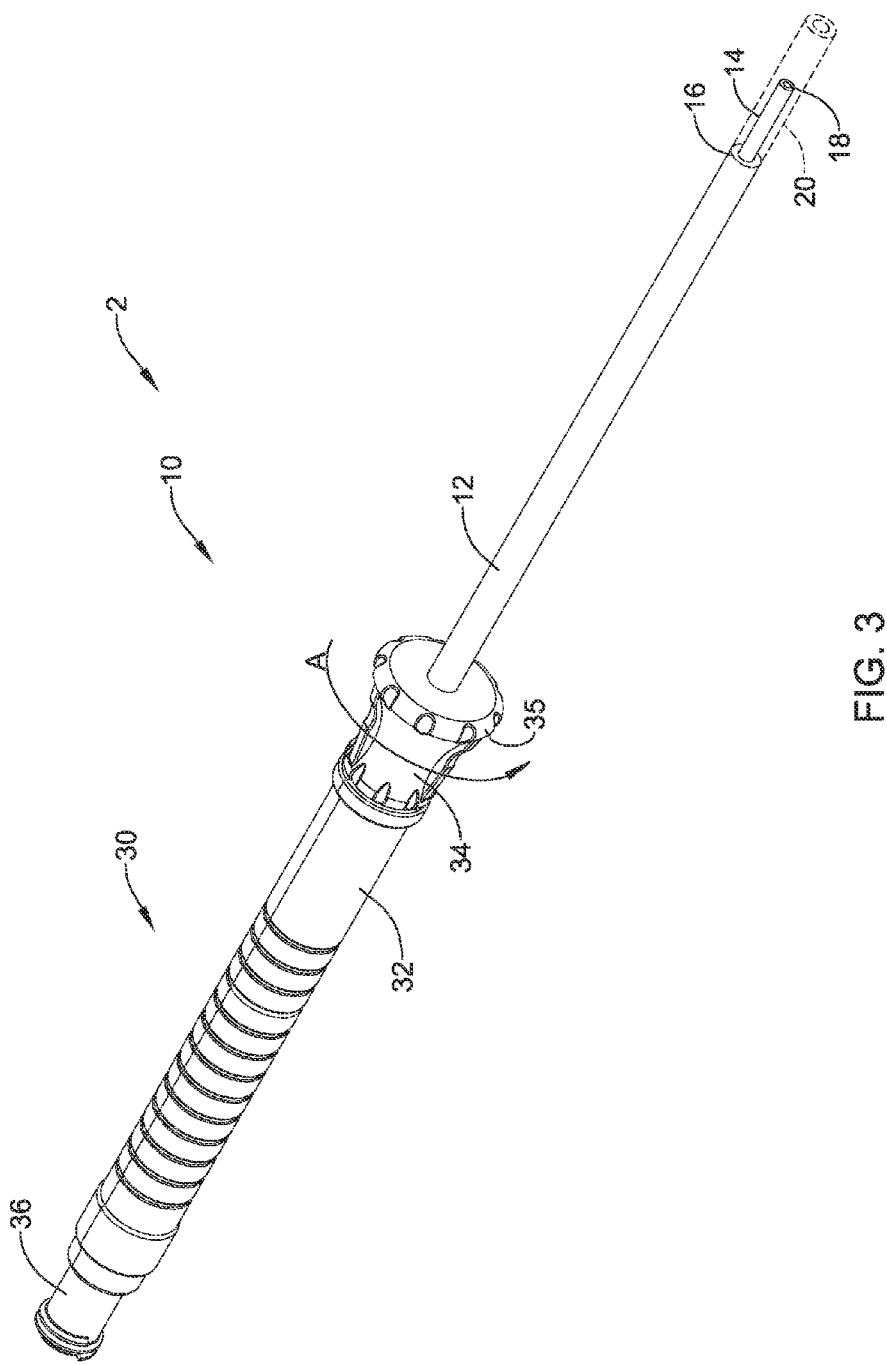
FIG. 3 is a perspective view of the stent delivery system of FIG. 1 manipulated during stent deployment.

Turning to FIG. 3, after the stent 20 has been positioned in a desired location in a body lumen, the user may actuate the locking mechanism 50 from the locked position to the unlocked position. For example, the user may rotate the knob 35 of the actuator 34 relative to the handle 32 about the longitudinal axis of the device, as shown by arrow A. In some instances, the user may grasp the handle 32 with the palm of one hand while also rotating the knob 35 of the actuator 34 with the fingers of the same hand, permitting one-handed actuation of the actuator 34.

Figure 4:
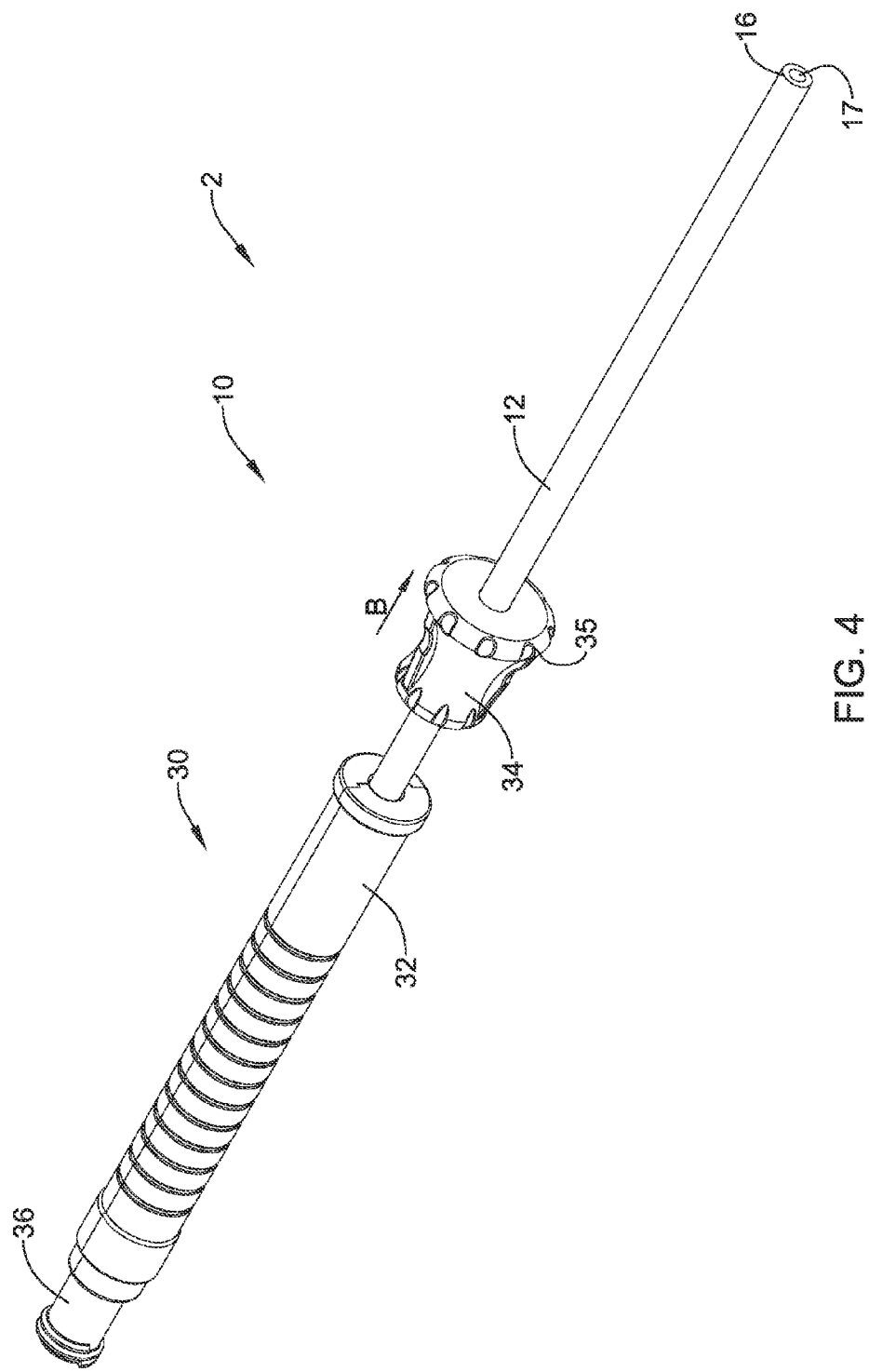
FIG. 4 is a perspective view of the stent delivery system of FIG. 1 further manipulated during stent deployment.

With the actuator 34 in the unlocked position, the knob 35 of the actuator 34 may be moved distally relative to the handle 32 along the longitudinal axis of the device as shown by arrow B, and thus move the outer tubular member 12 distally relative to the inner member 14 to the second position, shown in FIG. 4.

Figure 4A:
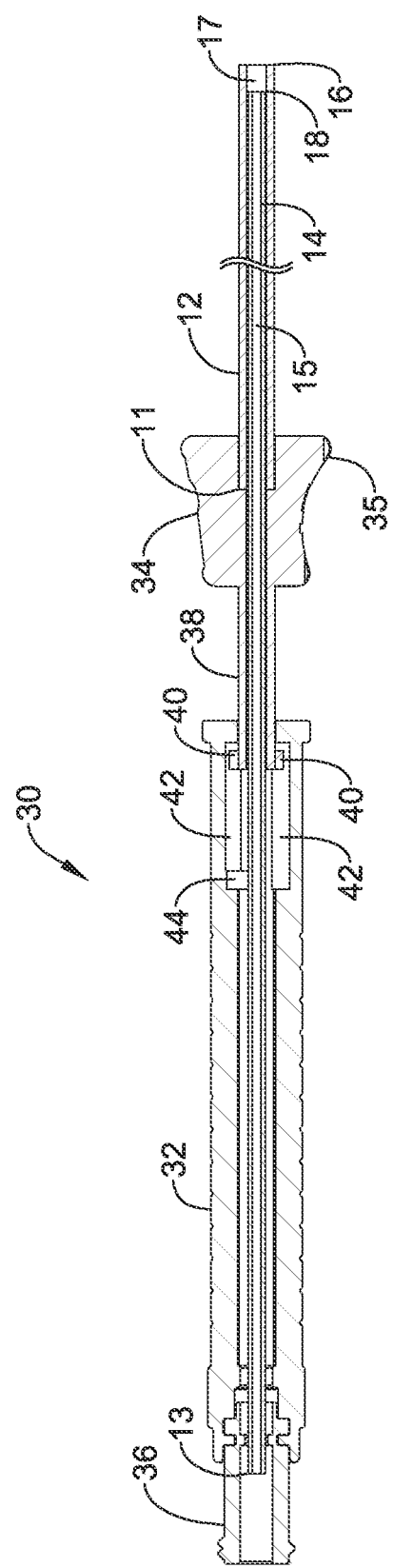
FIG. 4A is a longitudinal cross-sectional view of the stent delivery system of FIG. 4.

As shown in FIG. 4A, the protrusions 40 may be aligned with and move distally through the longitudinal portions 46 of the channels 42 to the second position. In some instances, the user may grasp the handle 32 with the palm of one hand while also moving the knob 35 of the actuator 34 distally with the fingers of the same hand, permitting one-handed actuation of the actuator 34 to the second position. Moving the stent delivery device 10 to the second position may position the distal end 16 of the outer tubular member 12 even with or distal of the distal end 18 of the inner member 14 to deploy the stent 20. Accordingly, moving the locking mechanism 50 from the locked position to the unlocked position and subsequently actuating the actuator 34 from the first position to the second position to deploy the stent 20 may be performed with a single hand of an operator.

Figure 5:
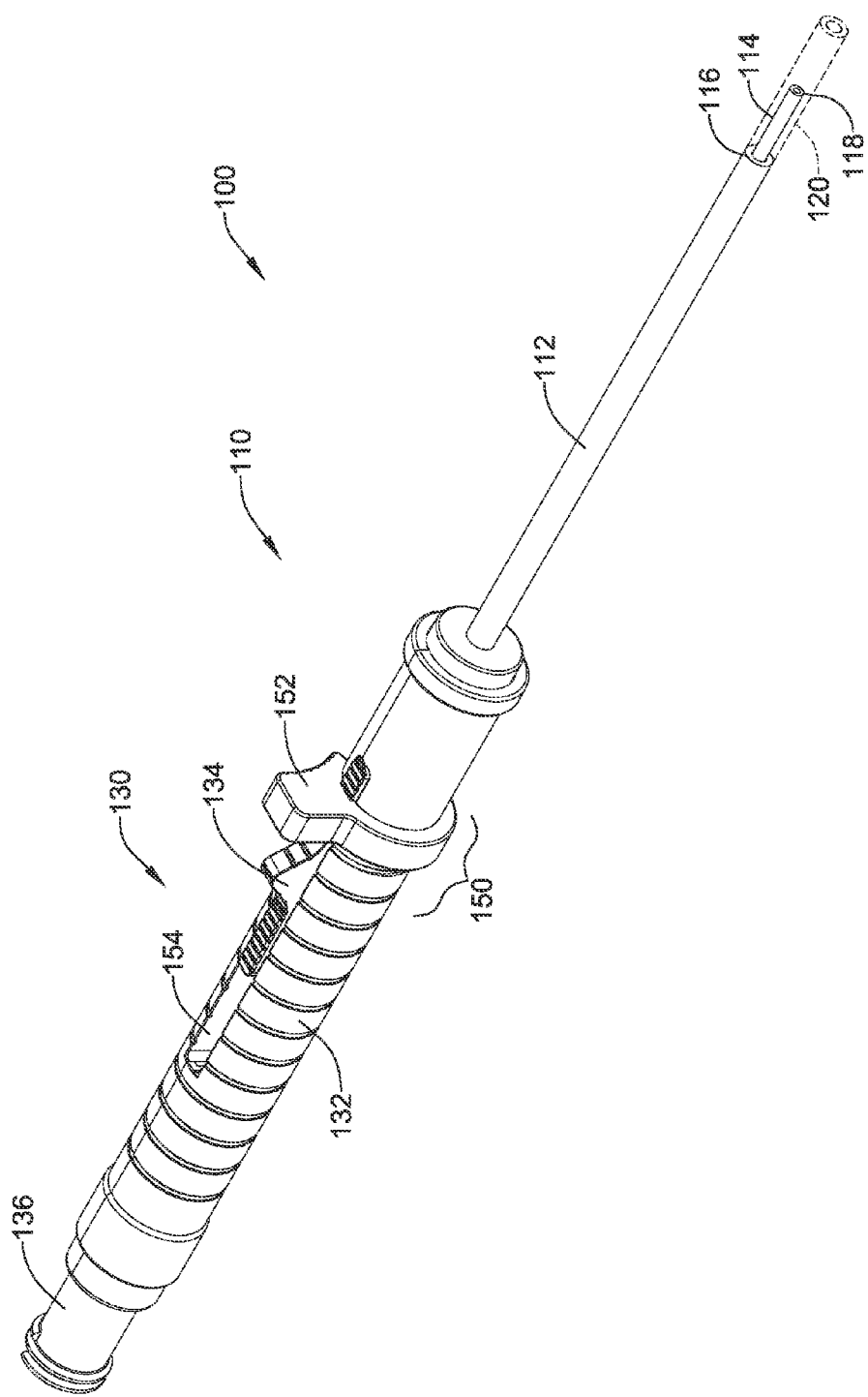
FIG. 5 is a perspective view of another exemplary stent delivery system in accordance with this disclosure.
Figure 5A:
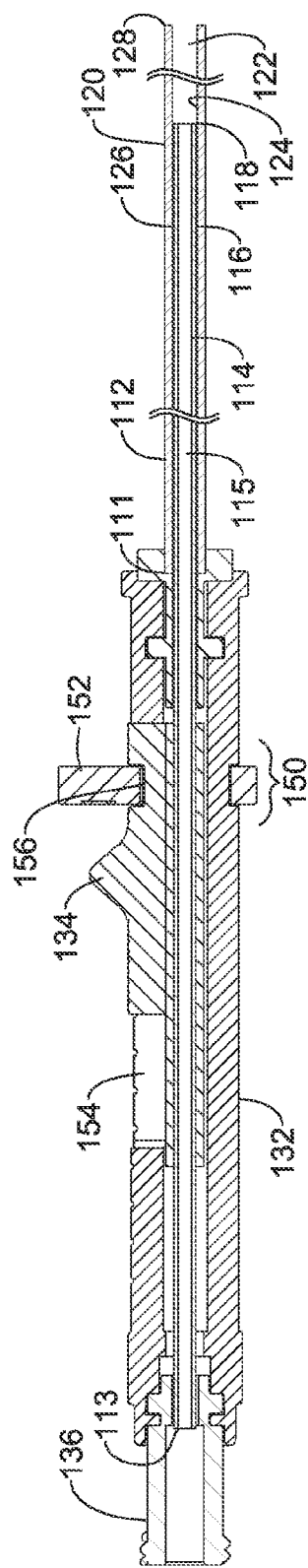
FIG. 5A is a longitudinal cross-sectional view of the stent delivery system of FIG. 5.

Another exemplary stent delivery system 100 is illustrated in FIGS. 5 through 7A. The stent delivery system 100 may include a stent delivery device 110 configured to deliver a stent 120 (shown in phantom), such as a ureteral stent, to a body lumen. The stent delivery system 100 is shown in a first position in FIGS. 5 and 5A. The stent delivery device 110 may include an outer tubular member 112, an inner elongate member 114 extending through the lumen 117 of the outer tubular member 112, and a handle assembly 130.

The outer tubular member 112, which may have a proximal end 111 coupled to and/or positioned in the handle assembly 130, may extend distally from the handle assembly 130 along a longitudinal axis to a distal end 116 of the outer tubular member 112. Furthermore, the elongate inner member 114, which may have a proximal end 113 coupled to and/or positioned in the handle assembly 130, may extend distally from the handle assembly 130 along the longitudinal axis to a distal end 118 of the elongate inner member 114. In some instances, the elongate inner member 114 may be a tubular member having a lumen 115 extending therethrough from the proximal end 113 to the distal end 118 of the elongate inner member 114. The lumen 115 may be sized to accommodate a guidewire therethrough such that the stent delivery device 110 and associated stent 120 may be advanced through a body lumen over a guidewire.

The stent 120 may be disposed proximate the distal end of the stent delivery device 110 for delivery to a body lumen. The stent 120 may be a tubular stent having a proximal end 126, a distal end 128, and a lumen 122 extending therethrough from the proximal end 126 to the distal end 128. In some instances, the stent 120 may be positionable on and surround a distal end region of the elongate inner member 114 in the first position. The distal end region of the elongate inner member 114 may extend distal of the distal end 116 of the outer tubular member 112 in the first position, with the stent 120 positioned distal of the outer tubular member 112. For example, the proximal end 126 of the stent 120 may abut the distal end 116 of the outer tubular member 112 when the stent 120 is secured to the stent delivery device 110 in the first position. In some instances the outer diameter of the distal end region of the elongate inner member 114 may be sized slightly larger than the inner diameter of the stent 120 such that the distal end region of the elongate inner member 114 frictionally engages the inner surface 124 of the stent 120 to secure the stent 120 onto the distal end region of the elongate inner member 114. As discussed later herein, actuation of the outer tubular member 112 distally relative to the inner member 114 may overcome the frictional force to deploy the stent 120 from the inner member 114. In other embodiments, the stent 120 may be secured to the stent delivery device 110 in other ways. For example, in some instances, the stent 120 may surround a distal end region of the inner member 114 while positioned within the lumen of the outer tubular member 112. In such an embodiment, the stent 120 may be expelled from the distal end of the outer tubular member 112 via relative longitudinal movement of the inner and outer members to deploy the stent 120.

The handle assembly 130 may include a handle 132 to be grasped by a user and an actuator 134 movable by a user relative to the handle 132. The handle 132 may be attached, such as fixedly secured, to one of the inner member 114 and the outer tubular member 112, and the actuator 134 may be attached, such as fixedly secured, to the other of the inner member 114 and the outer tubular member 112. The actuator 134 may be slidably positioned in the channel 154 of the handle 134 such that longitudinal movement of the actuator 134 in the channel 154 moves the inner member 114 longitudinally with respect to the outer tubular member 112. Accordingly, actuation of the actuator 134 relative to the handle 132 may correspondingly move the inner member 114 relative to the outer tubular member 112. For example, longitudinal movement of the actuator 134 along the longitudinal axis relative to the handle 132 may move the inner member 114 longitudinally relative to the outer tubular member 112. As discussed further herein, actuation of the actuator 134 relative to the handle 132 between the first position (FIG. 5) to a second position (FIG. 7) may cause axial movement of the outer tubular member 112 relative to the inner member 114 to deploy the stent 120 (e.g., move the inner member 114 proximally and/or move the outer member 112 distally). In the illustrated embodiment, the actuator 134 is fixedly secured to the inner member 114 and the handle 132 is fixedly secured to the outer tubular member 112. However, in other embodiments, the actuator 134 may be fixedly secured to the outer tubular member 112 and the handle 132 may be fixedly secured to the inner member 114, if desired.

The handle assembly 130 may also include a locking mechanism 150 for restricting actuation of the actuator 134 in the channel 154 from the first position to the second position. For example, the locking mechanism 150 may have a locked position in which the actuator 134 is prevented from moving from the first position to the second position and an unlocked position in which the actuator 134 is permitted to move from the first position to the second position.

The locking mechanism 150 may include a locking member 152 configured to selectively lock the actuator 134 with respect to the handle 132. For example, in a locked position (shown in FIGS. 5 and 5A), the locking member 152 may be engaged in a recess 156 of the actuator 134, or otherwise engaged with the actuator 134, thereby preventing the actuator 134 from moving longitudinally in the channel 154 of the handle 132. The locking member 152 may be selectively actuated by a user to an unlocked position (shown in FIGS. 6 and 6A) to permit the actuator 134 to move longitudinally in the channel 154. In the illustrated embodiment, the locking member 152 may be rotated about the longitudinal axis of the device from the locked position to the unlocked position, as shown by arrow A in FIG. 6. However, in other embodiments, the locking member 152 may be moved transverse to the longitudinal axis of the device, moved longitudinally parallel to the longitudinal axis of the device, or otherwise moved relative to the actuator 134 to the unlocked position. Accordingly, the locking member 152 may be movable independent of the actuator 134 such that the user must move the locking member 152 from the locked position to the unlocked position prior to moving the actuator 134 from the first position to the second position.

The locking member 152 may be a generally annular member circumferentially surrounding the handle 132, for instance. For example, the locking member 152 may be positioned in an annular groove or recess circumferentially around the handle 132. Alternatively, the handle 132 may include an annular protrusion or a plurality of discontinuous protrusions extending radially outward into a circumferential annular groove or recess in the locking member 152.

Figure 6:
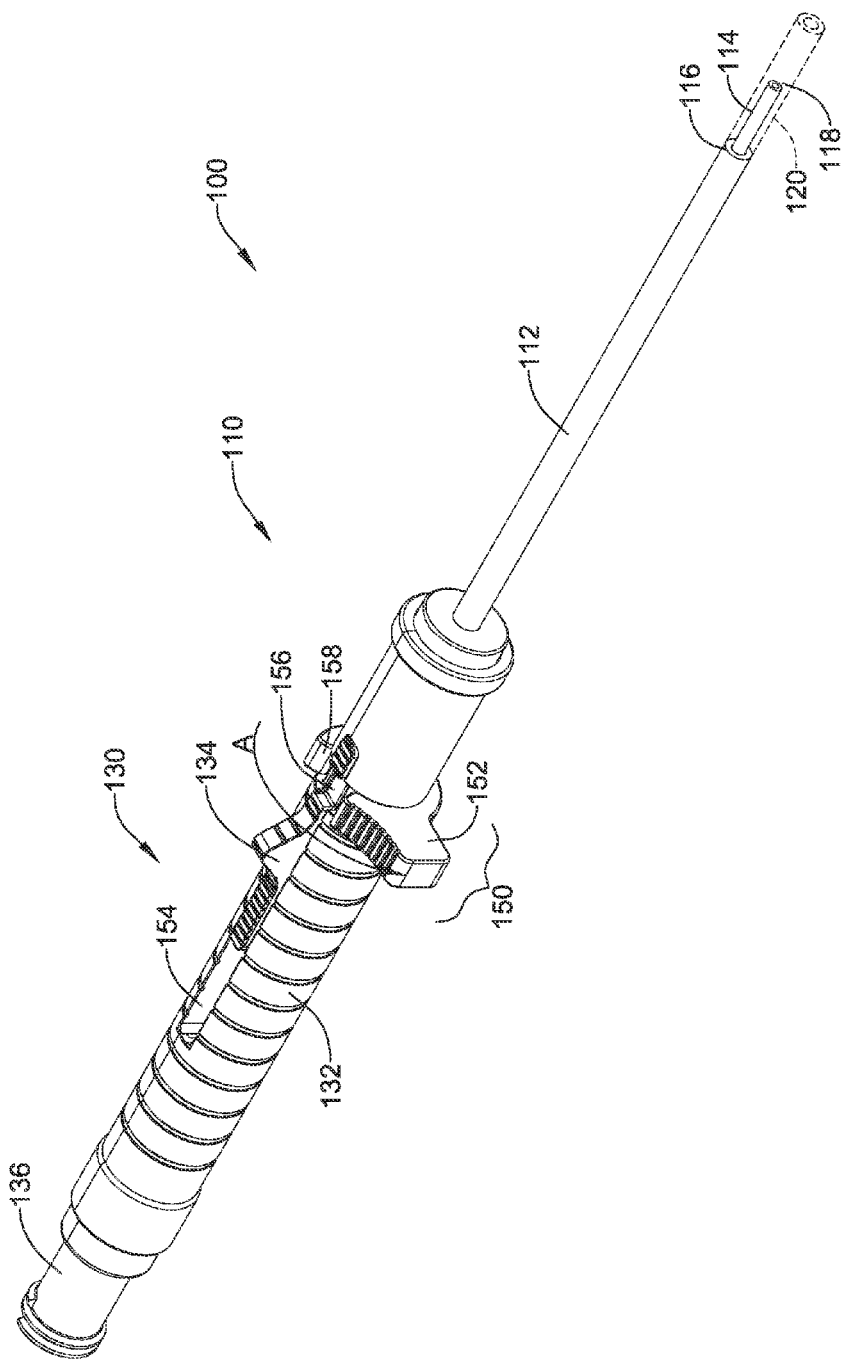
FIG. 6 is a perspective view of the stent delivery system of FIG. 5 manipulated during stent deployment.
Figure 6A:
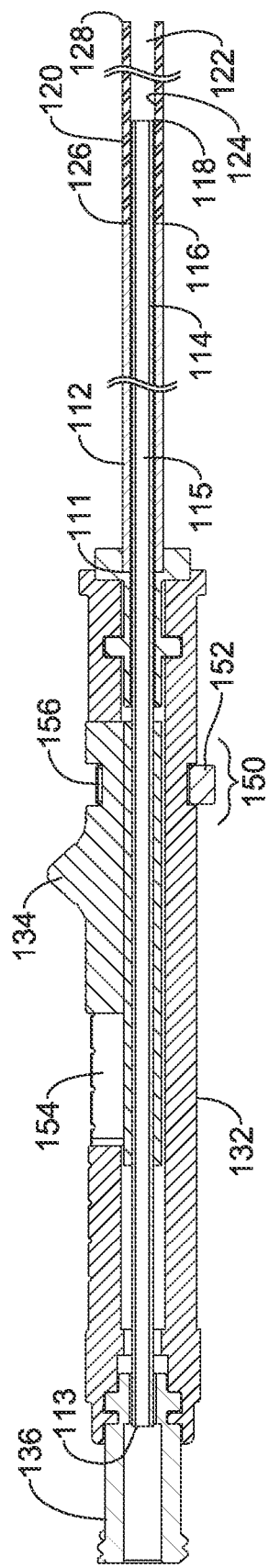
FIG. 6A is a longitudinal cross-sectional view of the stent delivery system of FIG. 6.

In some instances, the locking member 152 may be a discontinuous annular ring including an opening 158 extending from a radially outer surface to a radially inner surface of the locking member 152. In the locked position, shown in FIG. 5, the opening 158 may not be aligned with the channel 154 (e.g., out of alignment with channel 154), whereas in the unlocked position, shown in FIG. 6, the opening 158 may be aligned with the channel 154, permitting the actuator 134 to move through the opening 158 along the channel 154. Furthermore, the actuator 134 may include a recess 156 or other engagement structure in which a portion of the locking member 152 engages in the locked position. As shown in FIGS. 6 and 6A, as the locking member 152 is moved to the unlocked position, the locking member 152 may move out of the recess 156 or other engagement structure of the actuator 134.

The locking mechanism 150 may be configured such that when the locking member 152 is engaged in the recess 156 and/or the opening 158 is not aligned with the channel 154 (i.e., the locked position), the actuator 134 may be prevented from moving from the first position to the second position. When the locking member 152 is rotated such that the locking member 152 is disengaged from the recess 156 and/or the opening 158 is rotated into longitudinal alignment with the channel 154 (i.e., in the unlocked position) the actuator 134 may be permitted to move from the first position to the second position as the actuator 134 moves longitudinally in the channel 154. Thus, longitudinal movement of the outer tubular member 112 relative to the inner member 114 is precluded in the locked position and permitted in the unlocked position.

Thus, after the stent 120 has been positioned in a desired location in a body lumen, the user may actuate the locking mechanism 150 from the locked position to the unlocked position. For example, the user may rotate the locking member 152 relative to the handle 132 and actuator 134 about the longitudinal axis of the device until the opening 158 is aligned with the channel 156. In some instances, the user may grasp the handle 132 with the palm of one hand while also rotating the locking member 152 with the fingers of the same hand, permitting one-handed actuation of the locking member 152.

Figure 7:
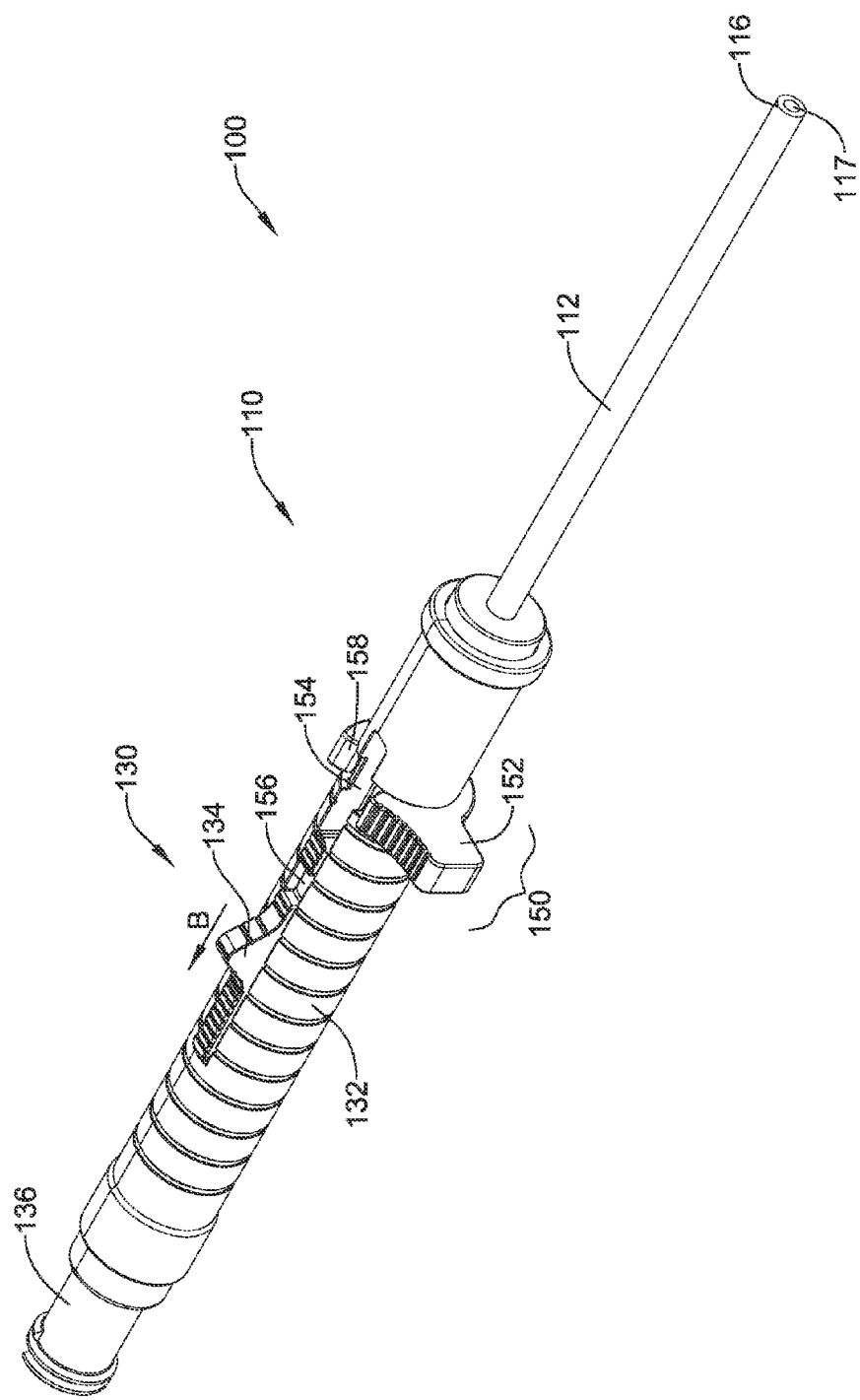
FIG. 7 is a perspective view of the stent delivery system of FIG. 5 manipulated during stent deployment.
Figure 7A:
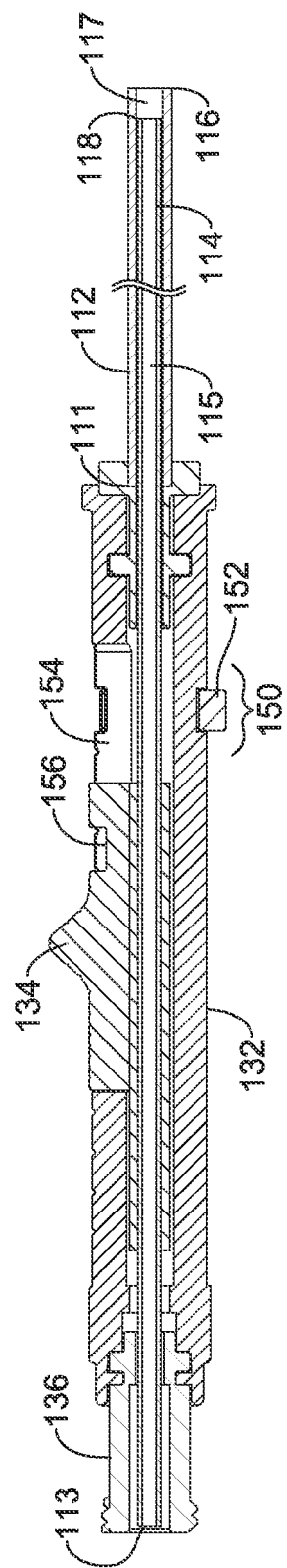
FIG. 7A is a longitudinal cross-sectional view of the stent delivery system of FIG. 7.

With the locking mechanism 150 in the unlocked position, the actuator 134 may be moved proximally relative to the handle 132 through the channel 154 along the longitudinal axis of the device, illustrated by arrow B, and thus move the inner member 114 proximally relative to the outer tubular member 112 to the second position, shown in FIGS. 7 and 7A. In some instances, the user may grasp the handle 132 with the palm of one hand while also moving the actuator 134 proximally with the fingers of the same hand, permitting one-handed actuation of the actuator 134 to the second position. Moving the stent delivery device 110 to the second position may position the distal end 116 of the outer tubular member 112 even with or distal of the distal end 118 of the inner member 114 to deploy the stent 120. Accordingly, moving the locking mechanism 150 from the locked position to the unlocked position and subsequently actuating the actuator 134 from the first position to the second position to deploy the stent 120 may be performed with a single hand of an operator.

Figure 8:
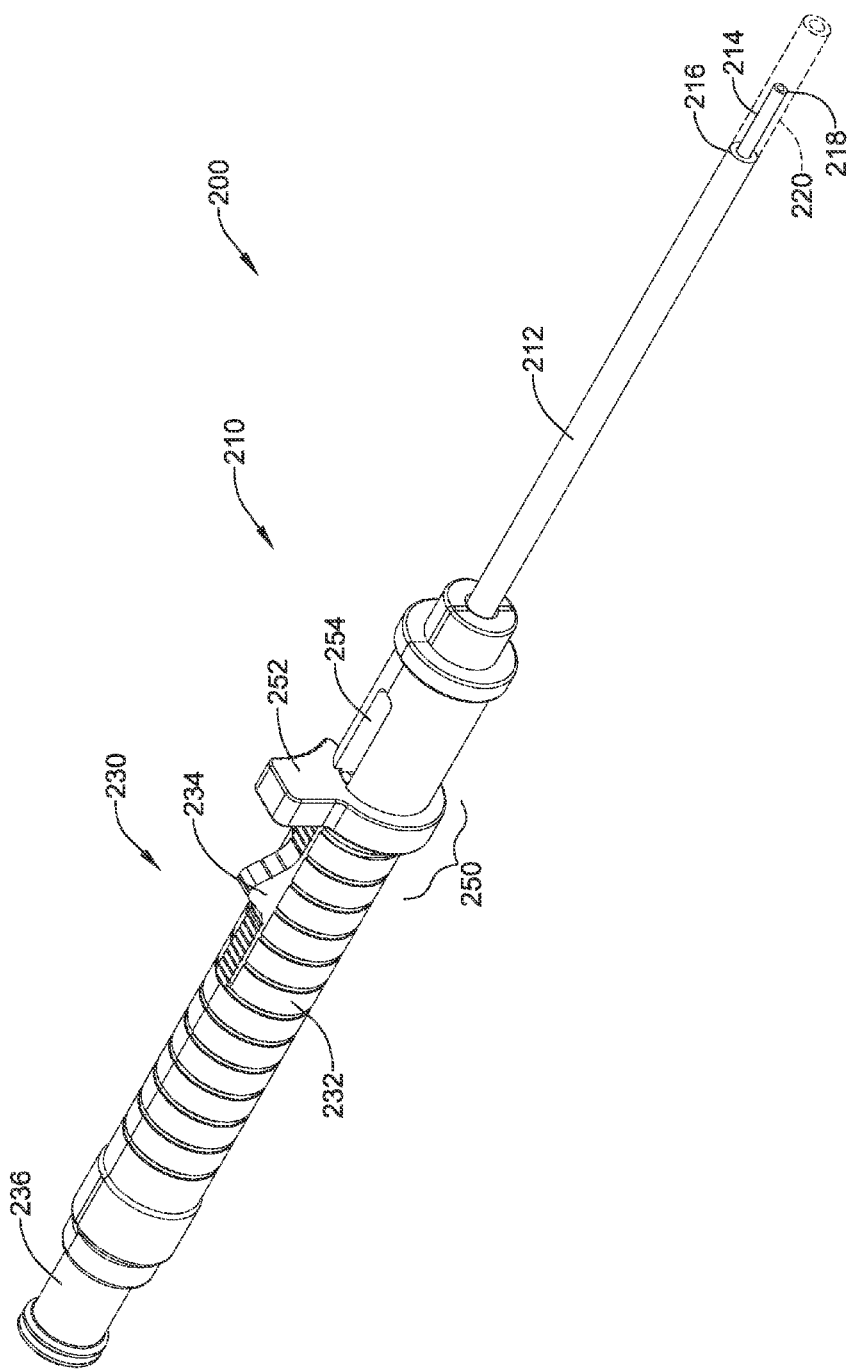
FIG. 8 is a perspective view of another exemplary stent delivery system in accordance with this disclosure.
Figure 8A:
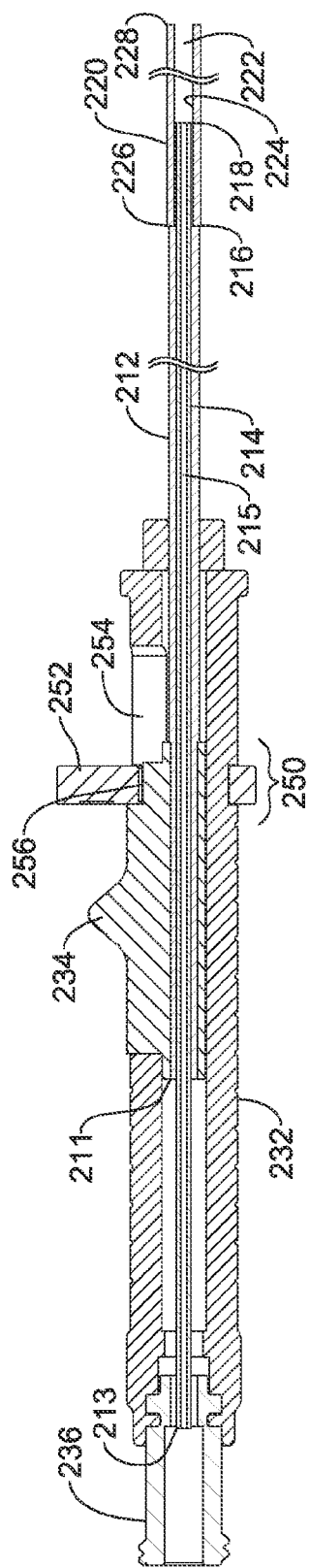
FIG. 8A is a longitudinal cross-sectional view of the stent delivery system of FIG. 8.

Another exemplary stent delivery system 200 is illustrated in FIGS. 8 through 10A. In many respects, the stent delivery system 200 may be similar to the stent delivery system 100. The stent delivery system 200 may include a stent delivery device 210 configured to deliver a stent 220 (shown in phantom), such as a ureteral stent, to a body lumen. The stent delivery system 200 is shown in a first position in FIGS. 8 and 8A. The stent delivery device 210 may include an outer tubular member 212, an inner elongate member 214 extending through the lumen 217 of the outer tubular member 212, and a handle assembly 230.

The outer tubular member 212, which may have a proximal end 211 coupled to and/or positioned in the handle assembly 230, may extend distally from the handle assembly 230 along a longitudinal axis to a distal end 216 of the outer tubular member 212. Furthermore, the elongate inner member 214, which may have a proximal end 213 coupled to and/or positioned in the handle assembly 230, may extend distally from the handle assembly 230 along the longitudinal axis to a distal end 218 of the elongate inner member 214. In some instances, the elongate inner member 214 may be a tubular member having a lumen 215 extending therethrough from the proximal end 213 to the distal end 218 of the elongate inner member 214. The lumen 215 may be sized to accommodate a guidewire therethrough such that the stent delivery device 210 and associated stent 220 may be advanced through a body lumen over a guidewire.

The stent 220 may be disposed proximate the distal end of the stent delivery device 210 for delivery to a body lumen. The stent 220 may be a tubular stent having a proximal end 226, a distal end 228, and a lumen 222 extending therethrough from the proximal end 226 to the distal end 228. In some instances, the stent 220 may be positionable on and surround a distal end region of the elongate inner member 214 in the first position. The distal end region of the elongate inner member 214 may extend distal of the distal end 216 of the outer tubular member 212 in the first position, with the stent 220 positioned distal of the outer tubular member 212. For example, the proximal end 226 of the stent 220 may abut the distal end 216 of the outer tubular member 212 when the stent 220 is secured to the stent delivery device 210 in the first position. In some instances the outer diameter of the distal end region of the elongate inner member 214 may be sized slightly larger than the inner diameter of the stent 220 such that the distal end region of the elongate inner member 214 frictionally engages the inner surface 224 of the stent 220 to secure the stent 220 onto the distal end region of the elongate inner member 214. As discussed later herein, actuation of the outer tubular member 212 distally relative to the inner member 214 may overcome the frictional force to deploy the stent 220 from the inner member 214. In other embodiments, the stent 220 may be secured to the stent delivery device 210 in other ways. For example, in some instances, the stent 220 may surround a distal end region of the inner member 214 while positioned within the lumen of the outer tubular member 212. In such an embodiment, the stent 220 may be expelled from the distal end of the outer tubular member 212 via relative longitudinal movement of the inner and outer members to deploy the stent 220.

The handle assembly 230 may include a handle 232 to be grasped by a user and an actuator 234 movable by a user relative to the handle 232. The handle 232 may be attached, such as fixedly secured, to one of the inner member 214 and the outer tubular member 212, and the actuator 234 may be attached, such as fixedly secured, to the other of the inner member 214 and the outer tubular member 212. The actuator 234 may be slidably positioned in the channel 254 of the handle 234 such that longitudinal movement of the actuator 234 in the channel 254 moves the inner member 214 longitudinally with respect to the outer tubular member 212. Accordingly, actuation of the actuator 234 relative to the handle 232 may correspondingly move the inner member 214 relative to the outer tubular member 212. For example, longitudinal movement of the actuator 234 along the longitudinal axis relative to the handle 232 may move the outer tubular member 212 longitudinally relative to the inner member 214. As discussed further herein, actuation of the actuator 234 relative to the handle 232 between the first position (FIG. 8) to a second position (FIG. 10) may cause axial movement of the outer tubular member 212 relative to the inner member 214 to deploy the stent 220 (e.g., move the inner member 214 proximally and/or move the outer member 212 distally). In the illustrated embodiment, the actuator 234 is fixedly secured to the outer tubular member 212 and the handle 232 is fixedly secured to the inner member 214. However, in other embodiments, the actuator 234 may be fixedly secured to the inner member 214 and the handle 232 may be fixedly secured to the outer tubular member 212, if desired.

The handle assembly 230 may also include a locking mechanism 250 for restricting actuation of the actuator 234 in the channel 254 from the first position to the second position. For example, the locking mechanism 250 may have a locked position in which the actuator 234 is prevented from moving from the first position to the second position and an unlocked position in which the actuator 234 is permitted to move from the first position to the second position.

The locking mechanism 250 may include a locking member 252 configured to selectively lock the actuator 234 with respect to the handle 232. For example, in a locked position (shown in FIGS. 8 and 8A), the locking member 252 may be engaged in a recess 256 of the actuator 234, or otherwise engaged with the actuator 234, thereby preventing the actuator 234 from moving longitudinally in the channel 254 of the handle 232. The locking member 252 may be selectively actuated by a user to an unlocked position (shown in FIGS. 9 and 9A) to permit the actuator 234 to move longitudinally in the channel 254. In the illustrated embodiment, the locking member 252 may be rotated about the longitudinal axis of the device from the locked position to the unlocked position, as shown by arrow A in FIG. 9. However, in other embodiments, the locking member 252 may be moved transverse to the longitudinal axis of the device, moved longitudinally parallel to the longitudinal axis of the device, or otherwise moved relative to the actuator 234 to the unlocked position. Accordingly, the locking member 252 may be movable independent of the actuator 234 such that the user must move the locking member 252 from the locked position to the unlocked position prior to moving the actuator 234 from the first position to the second position.

The locking member 252 may be a generally annular member circumferentially surrounding the handle 232, for instance. For example, the locking member 252 may be positioned in an annular groove or recess circumferentially around the handle 232. Alternatively, the handle 232 may include an annular protrusion or a plurality of discontinuous protrusions extending radially outward into a circumferential annular groove or recess in the locking member 252.

Figure 9:
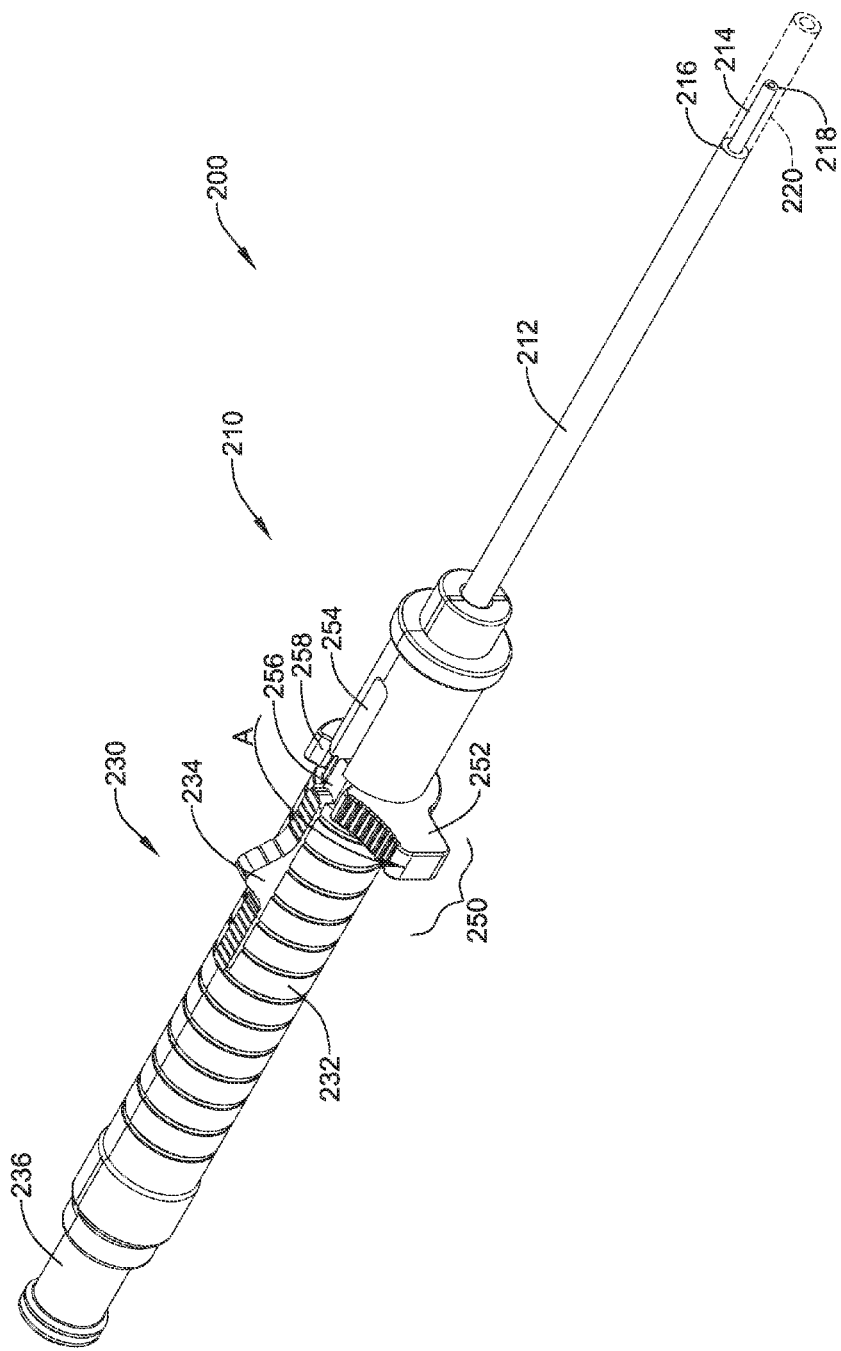
FIG. 9 is a perspective view of the stent delivery system of FIG. 8 manipulated during stent deployment.
Figure 9A:
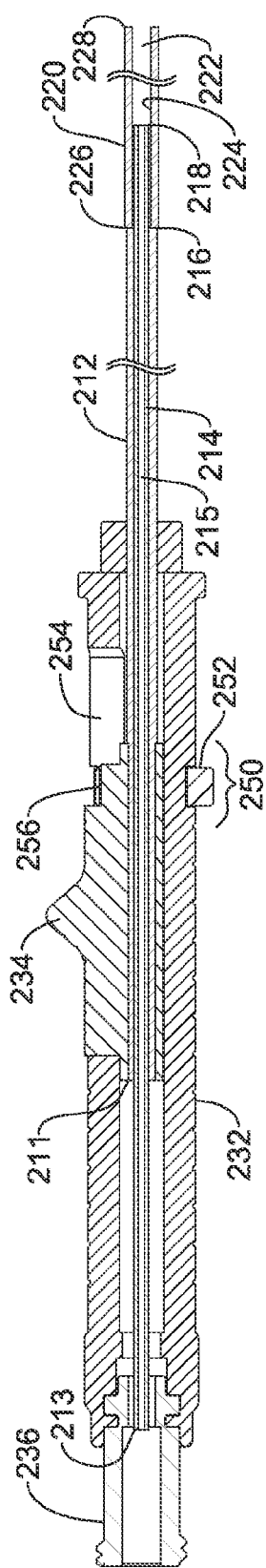
FIG. 9A is a longitudinal cross-sectional view of the stent delivery system of FIG. 9.

In some instances, the locking member 252 may be a discontinuous annular ring including an opening 258 extending from a radially outer surface to a radially inner surface of the locking member 252. In the locked position, shown in FIG. 8, the opening 258 may not be aligned with the channel 254 (e.g., out of alignment with the channel 254), whereas in the unlocked position, shown in FIG. 9, the opening 258 may be aligned with the channel 254, permitting the actuator 234 to move through the opening 258 along the channel 254. Furthermore, the actuator 234 may include a recess 256 or other engagement structure in which a portion of the locking member 252 engages in the locked position. As shown in FIGS. 9 and 9A, as the locking member 252 is moved to the unlocked position, the locking member 252 may move out of the recess 256 or other engagement structure of the actuator 234.

The locking mechanism 250 may be configured such that when the locking member 252 is engaged in the recess 256 and/or the opening 258 is not aligned with the channel 254 (i.e., the locked position), the actuator 234 may be prevented from moving from the first position to the second position. When the locking member 252 is rotated such that the locking member 252 is disengaged from the recess 256 and/or the opening 258 is rotated into longitudinal alignment with the channel 254 (i.e., in the unlocked position) the actuator 234 may be permitted to move from the first position to the second position as the actuator 234 moves longitudinally in the channel 254. Thus, longitudinal movement of the outer tubular member 212 relative to the inner member 214 is precluded in the locked position and permitted in the unlocked position.

Thus, after the stent 220 has been positioned in a desired location in a body lumen, the user may actuate the locking mechanism 250 from the locked position to the unlocked position. For example, the user may rotate the locking member 252 relative to the handle 232 and actuator 234 about the longitudinal axis of the device until the opening 258 is aligned with the channel 256. In some instances, the user may grasp the handle 232 with the palm of one hand while also rotating the locking member 252 with the fingers of the same hand, permitting one-handed actuation of the locking member 252.

Figure 10:
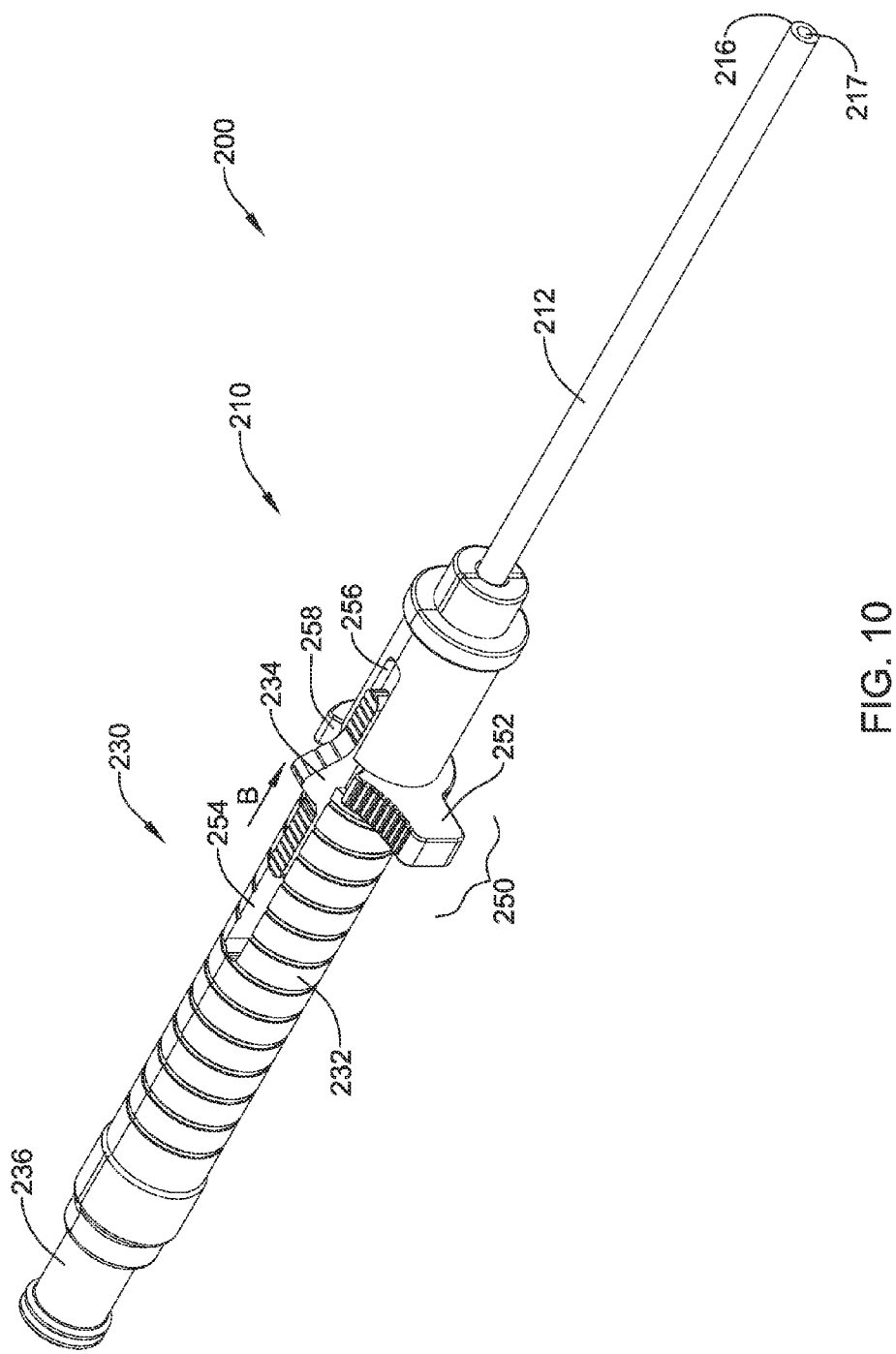
FIG. 10 is a perspective view of the stent delivery system of FIG. 8 manipulated during stent deployment.
Figure 10A:
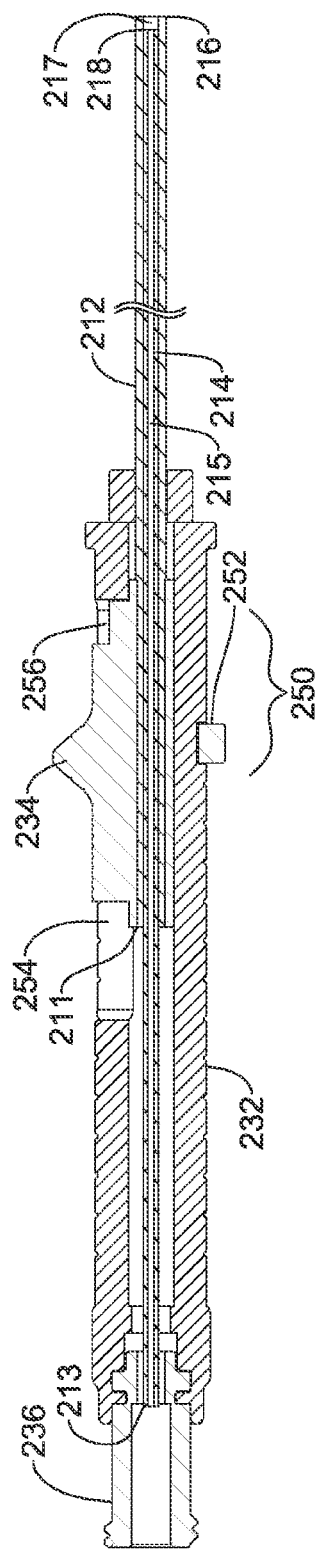
FIG. 10A is a longitudinal cross-sectional view of the stent delivery system of FIG. 10.

With the locking mechanism 250 in the unlocked position, the actuator 234 may be moved distally relative to the handle 232 through the channel 254 along the longitudinal axis of the device, illustrated by arrow B, and thus move the outer tubular member 212 distally relative to the inner member 214 to the second position, shown in FIGS. 10 and 10A. In some instances, the user may grasp the handle 232 with the palm of one hand while also moving the actuator 234 distally with the fingers of the same hand, permitting one-handed actuation of the actuator 234 to the second position. Moving the stent delivery device 210 to the second position may position the distal end 216 of the outer tubular member 212 even with or distal of the distal end 218 of the inner member 214 to deploy the stent 220. Accordingly, moving the locking mechanism 250 from the locked position to the unlocked position and subsequently actuating the actuator 234 from the first position to the second position to deploy the stent 220 may be performed with a single hand of an operator.

Another exemplary stent delivery system 300 is illustrated in FIGS. 11A and 11B. The stent delivery system 300 may include a stent delivery device 310 configured to deliver a stent 320, such as a ureteral stent, to a body lumen. The stent delivery system 300 is shown in a first position in FIG. 11A and in a second position in FIG. 11B. The stent delivery device 310 may include an outer tubular member 312, an inner elongate member 314 extending through the lumen of the outer tubular member 312, and a handle assembly 330.

The outer tubular member 312, which may have a proximal end coupled to and/or positioned in the handle assembly 330, may extend distally from the handle assembly 330 along a longitudinal axis to a distal end 316 of the outer tubular member 312. Furthermore, the elongate inner member 314, which may have a proximal end coupled to and/or positioned in the handle assembly 330, may extend distally from the handle assembly 330 along the longitudinal axis to a distal end 318 of the elongate inner member 314. In some instances, the elongate inner member 314 may be a tubular member having a lumen extending therethrough from the proximal end to the distal end of the elongate inner member 314. The lumen may be sized to accommodate a guidewire therethrough such that the stent delivery device 310 and associated stent 320 may be advanced through a body lumen over a guidewire.

The stent 320 may be disposed proximate the distal end of the stent delivery device 310 for delivery to a body lumen. The stent 320 may be a tubular stent having a proximal end 326, a distal end 328, and a lumen 322 extending therethrough from the proximal end 326 to the distal end 328. In some instances, the stent 320 may be positionable on and surround a distal end region of the elongate inner member 314 in the first position. The distal end region of the elongate inner member 314 may extend distal of the distal end 316 of the outer tubular member 312 in the first position, with the stent 320 positioned distal of the outer tubular member 312. For example, the proximal end 326 of the stent 320 may abut the distal end 316 of the outer tubular member 312 when the stent 320 is secured to the stent delivery device 310 in the first position. In some instances the distal end region of the elongate inner member 314 may frictionally engage the stent 320 to secure the stent 320 thereon. As discussed later herein, actuation of the inner member 314 proximally relative to the outer tubular member 312 may overcome the frictional force to deploy the stent 320 from the inner member 314. In other embodiments, the stent 320 may be secured to the stent delivery device 310 in other ways, such as those discussed above.

The handle assembly 330 may include a handle 332 to be grasped by a user and an actuator 334 movable by a user relative to the handle 332. The handle 332 may be attached, such as fixedly secured, to one of the inner member 314 and the outer tubular member 312, and the actuator 334 may be attached, such as fixedly secured, to the other of the inner member 314 and the outer tubular member 312. The actuator 334 may be rotatably actuatable relative to the handle 334 such that rotational movement of the actuator 334 moves the inner member 314 longitudinally with respect to the outer tubular member 312. Accordingly, actuation of the actuator 334 relative to the handle 332 may correspondingly move the inner member 314 relative to the outer tubular member 312. As discussed further herein, rotational actuation of the actuator 334 relative to the handle 332 between the first position (FIG. 11A) to a second position (FIG. 11B) may cause axial movement of the outer tubular member 312 relative to the inner member 314 to deploy the stent 320 (e.g., move the inner member 314 proximally and/or move the outer member 312 distally). In the illustrated embodiment, the actuator 334 is fixedly secured to the inner member 314 and the handle 332 is fixedly secured to the outer tubular member 312. However, in other embodiments, the actuator 334 may be fixedly secured to the outer tubular member 312 and the handle 332 may be fixedly secured to the inner member 314, if desired.

The actuator 334 may be pivotably coupled to the handle 332 at a pivot point 374 such that the actuator 334 is rotatable about the pivot point 374. Furthermore, the actuator 334 may be coupled to the inner member 314 via a linkage at point 370. For example, the point 370, which may be a fixed point relative to the inner member 314, may travel along the slot 372 of the actuator 334 as the actuator 334 pivots about the pivot point 374 from the first position to the second position. Thus, rotation of the actuator 334 relative to the handle 332 may cause corresponding longitudinal movement of the inner member 314 relative to the handle 332.

After the stent 320 has been positioned in a desired location in a body lumen, the user may actuate (e.g., rotate) the actuator 334 relative to the handle 332 about the pivot point 374, and thus move the inner member 314 proximally relative to the outer tubular member 312 to the second position, shown in FIG. 11B. In some instances, the user may grasp the handle 332 with the palm of one hand while also rotating the actuator 334 with the fingers of the same hand, permitting one-handed actuation of the actuator 334 to the second position. Moving the stent delivery device 310 to the second position may position the distal end 316 of the outer tubular member 312 even with or distal of the distal end 318 of the inner member 314 to deploy the stent 320. Accordingly, actuating the actuator 334 from the first position to the second position to deploy the stent 320 may be performed with a single hand of an operator.

Figure 12A:
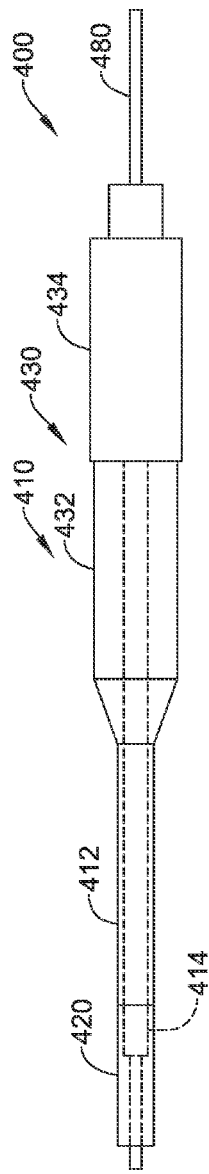
FIGS. 12A-12C are plan views of another stent delivery system illustrating stent deployment in accordance with this disclosure.
Figure 12B:
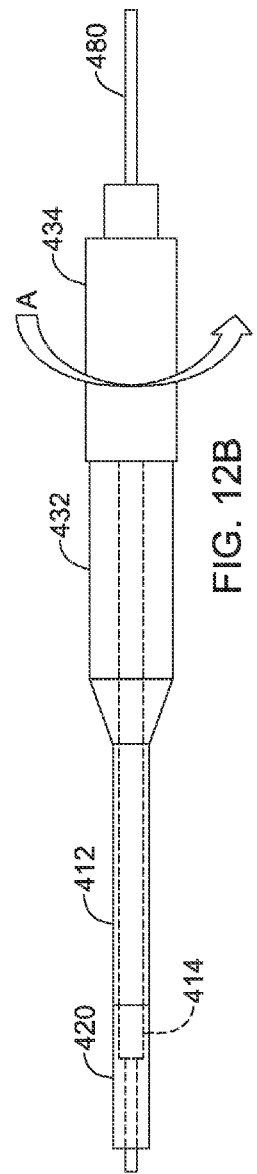
Figure 12C:
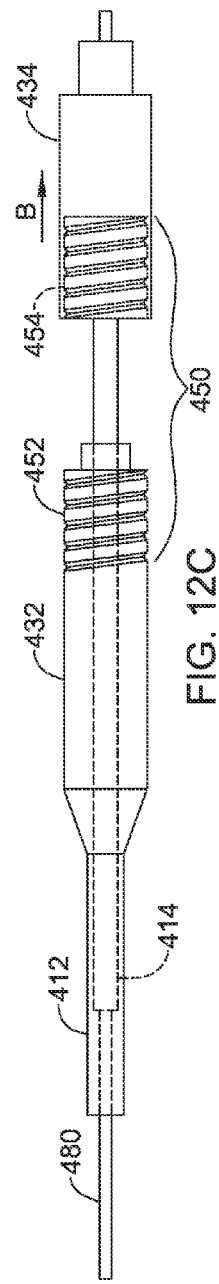

Another exemplary stent delivery system 400 is illustrated in FIGS. 12A through 12C. The stent delivery system 400 may include a stent delivery device 410 configured to deliver a stent 420, such as a ureteral stent, to a body lumen. The stent delivery system 400 is shown in a first position in FIG. 12A and in a second position in FIG. 12C. The stent delivery device 410 may include an outer tubular member 412, an inner elongate member 414 extending through the lumen of the outer tubular member 412, and a handle assembly 430.

The outer tubular member 412, which may have a proximal end coupled to and/or positioned in the handle assembly 430, may extend distally from the handle assembly 430 along a longitudinal axis to a distal end of the outer tubular member 412. Furthermore, the elongate inner member 414, which may have a proximal end coupled to and/or positioned in the handle assembly 430, may extend distally from the handle assembly 430 along the longitudinal axis to a distal end of the elongate inner member 414. In some instances, the elongate inner member 414 may be a tubular member having a lumen extending therethrough from the proximal end to the distal end of the elongate inner member 414. The lumen may be sized to accommodate a guidewire 480 therethrough such that the stent delivery device 410 and associated stent 420 may be advanced through a body lumen over the guidewire 480.

The stent 420 may be disposed proximate the distal end of the stent delivery device 410 for delivery to a body lumen. The stent 420 may be a tubular stent, similar to the stents described above. In some instances, the stent 420 may be positionable on and surround a distal end region of the elongate inner member 414 in the first position. The distal end region of the elongate inner member 414 may extend distal of the distal end of the outer tubular member 412 in the first position, with the stent 420 positioned distal of the outer tubular member 412. For example, the proximal end of the stent 420 may abut the distal end of the outer tubular member 412 when the stent 420 is secured to the stent delivery device 410 in the first position. In some instances the distal end region of the elongate inner member 414 may frictionally engage the stent 420 to secure the stent 420 thereon. As discussed later herein, actuation of the inner member 414 proximally relative to the outer tubular member 412 may overcome the frictional force to deploy the stent 420 from the inner member 414. In other embodiments, the stent 420 may be secured to the stent delivery device 410 in other ways, such as those discussed above.

The handle assembly 430 may include a handle 432 to be grasped by a user and an actuator 434 movable by a user relative to the handle 432. The handle 432 may be attached, such as fixedly secured, to one of the inner member 414 and the outer tubular member 412, and the actuator 434 may be attached, such as fixedly secured, to the other of the inner member 414 and the outer tubular member 412. The actuator 434 may be actuatable relative to the handle 434. Accordingly, actuation of the actuator 434 relative to the handle 432 may correspondingly move the inner member 414 relative to the outer tubular member 412. As discussed further herein, actuation of the actuator 434 relative to the handle 432 between the first position (FIG. 12A) to a second position (FIG. 12C) may cause axial movement of the outer tubular member 412 relative to the inner member 414 to deploy the stent 420 (e.g., move the inner member 414 proximally and/or move the outer member 412 distally). In the illustrated embodiment, the actuator 434 is fixedly secured to the inner member 414 and the handle 432 is fixedly secured to the outer tubular member 412. However, in other embodiments, the actuator 434 may be fixedly secured to the outer tubular member 412 and the handle 432 may be fixedly secured to the inner member 414, if desired.

The handle assembly 430 may also include a locking mechanism 450 for restricting actuation of the actuator 434 from the first position to the second position. For example, the locking mechanism 450 may have a locked position in which the actuator 434 is prevented from moving from the first position to the second position and an unlocked position in which the actuator 434 is permitted to move from the first position to the second position.

The locking mechanism 450 may include mating threaded portions of the actuator 434 and the handle 432. For example, the handle 432 may include a threaded region 452, such as a male threaded region, configured to threadably engage with a complementary threaded region 454, such as a female threaded region, of the actuator 434. It is noted that in other embodiments, the female threaded region may be provided with the handle 432 and the male threaded region may be provided with the actuator 434. Rotation of the actuator 434 relative to the handle 432 in a first rotational direction may cause the mating threaded regions 452, 454 to threadably engage, while rotation of the actuator 434 relative to the handle 432 in a second rotational direction may cause the mating threaded regions 452, 454 to threadably disengage.

The locking mechanism 450 may be configured such that when the mating threaded regions 452, 454 are threadably engaged (i.e., in the locked position) the actuator 434 may be prevented from moving longitudinally from the first position to the second position. When the mating threaded regions 452, 454 are threadably disengaged (i.e., in the unlocked position) the actuator 434 may be permitted to move from the first position to the second position to deploy the stent 420. Thus, longitudinal movement of the outer tubular member 412 relative to the inner member 414 is precluded in the locked position and permitted in the unlocked position.

Turning to FIG. 12B, after the stent 420 has been positioned in a desired location in a body lumen, the user may actuate the locking mechanism 450 from the locked position to the unlocked position. For example, the user may rotate the actuator 434 relative to the handle 432 about the longitudinal axis of the device, as shown by arrow A to disengage the mating threaded regions 452, 454.

With the actuator 434 in the unlocked position, the actuator 434 may be moved proximally relative to the handle 432 along the longitudinal axis of the device as shown by arrow B, and thus move the inner member 414 proximally relative to the outer tubular member 412 to the second position, shown in FIG. 12C, to deploy the stent 420.

Figure 13A:
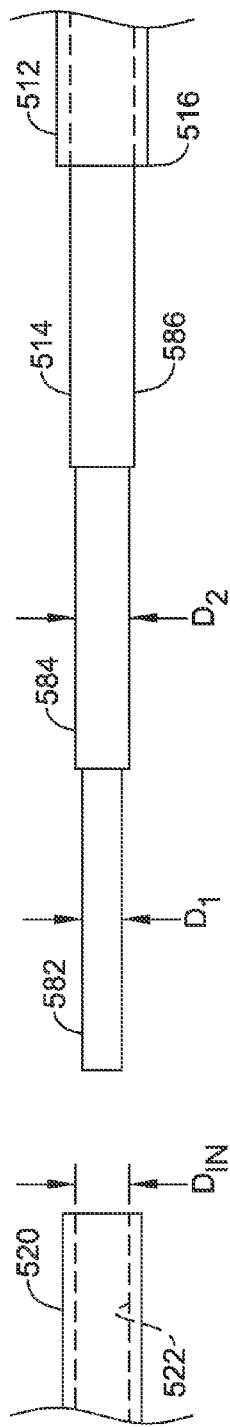
FIGS. 13A-13C are plan views of an exemplary stent securement structure for a stent delivery system.
Figure 13B:
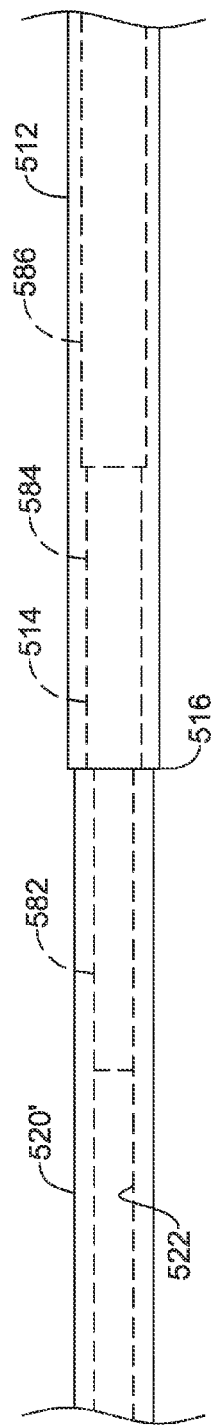
Figure 13C:
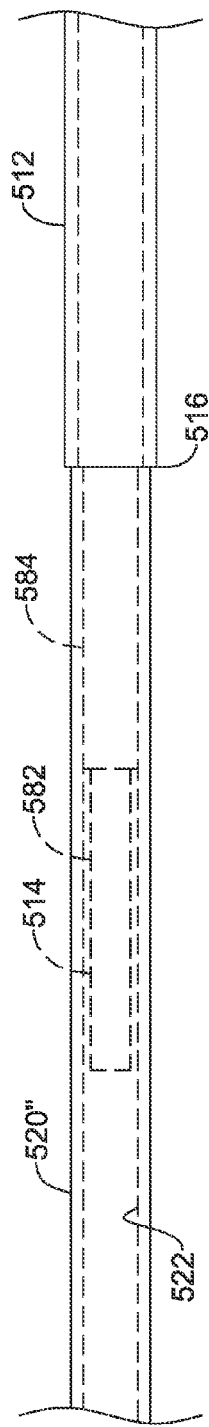

FIGS. 13A through 13C illustrate an exemplary stent securement structure for a stent delivery system that may be incorporated into one of the stent delivery systems described above or another stent delivery system, if desired. The distal portion of an outer tubular member 512 and an associated inner member 514 of a stent delivery device, with an associated stent 520 is depicted.

The inner member 514 may include a plurality of stent securement portions, configured to frictionally engage an interior of the stent 520. For example, the inner member 514 may include a first stent securement portion 582 having a first diameter D1 and a second stent securement portion 584 having a second diameter D2. The second diameter D2 of the second stent securement portion 584 may be greater than the first diameter D1 of the first stent securement portion 582. In some instances, the inner member 514 may include one or more additional stent securement portions, such as a third stent securement portion 586, having a third diameter different than (e.g., greater than) the first and second stent securement portions 582, 584. The first stent securement portion 582 may be positioned distal of the second stent securement portion 584, forming a stepwise transition in the outer diameter of the inner member 514.

The stent 520, which may be a tubular member having a lumen extending therethrough, may have an inner diameter $D_{IN}$ sized appropriately such that the inner surface 522 of the stent 520 frictionally engages one of the stent securement portions of the inner member 514. Since the inner member 514 may include a plurality of discrete stent securement portions of different diameters, the inner member 514 may be configured to accommodate a plurality of sizes of stents 520 having different inner diameters $D_{IN}$.

For example, as shown in FIG. 13B, a first stent 520' having a first inner diameter may frictionally engage the first stent securement portion 582 for securement thereon. The first inner diameter of the stent 520' may be selected to be less than the outer diameter of the first stent securement portion 582 to provide a desired frictional engagement. The outer tubular member 512 may then be positioned proximal of the stent 520' such that the distal end of the outer tubular member 512 abuts the proximal end of the stent 520'. Similar to that described above, distal movement of the outer tubular member 512 relative to the inner member 514 may overcome the frictional engagement to deploy the stent 520' from the inner member 514 (e.g., move the inner member 514 proximally and/or move the outer member 512 distally).

Furthermore, as shown in FIG. 13C, a second stent 520" having a second inner diameter, greater than the first inner diameter of the first stent 520', may pass over the first stent securement portion 582 and frictionally engage the second stent securement portion 584 for securement thereon. The second inner diameter of the stent 520″ may be selected to be less than the outer diameter of the second stent securement portion 582 to provide a desired frictional engagement. In some instances, the second inner diameter of the stent 520″ may be greater than the outer diameter of the first stent 520″ securement portion 582. The outer tubular member 512 may then be positioned proximal of the stent 520″ such that the distal end of the outer tubular member 512 abuts the proximal end of the stent 520″. Similar to that described above, distal movement of the outer tubular member 512 relative to the inner member 514 may overcome the frictional engagement to deploy the stent 520″ from the inner member 514.

In some instances, the stent 520′ may have an inner diameter of about 1.14 millimeters and the first stent securement portion 582 may have an outer diameter of about 1.0 millimeters, while the stent 520″ may have an inner diameter of about 1.22 millimeters and the second stent securement portion 584 may have an outer diameter of about 1.1 millimeters, for example. In other instances, the stent 520′ may have an inner diameter of about 1.45 millimeters and the first stent securement portion 582 may have an outer diameter of about 1.3 millimeters, while the stent 520″ may have an inner diameter of about 1.8 millimeters and the second stent securement portion 584 may have an outer diameter of about 1.65 millimeters, for example. In some instances, the inner diameter of the stent 520′ may be in the range of about 0.8 millimeters to about 2.5 millimeters, in the range of about 1.0 millimeters to about 2.0 millimeters, or in the range of about 1.0 millimeters to about 1.5 millimeters, and the inner diameter of the stent 520″ may be in the range of about 1.0 millimeters to about 3.0 millimeters, in the range of about 1.2 millimeters to about 2.0 millimeters, or in the range of about 1.2 millimeters to about 1.8 millimeters, for example, with the diameter of the stent 520″ being greater than the inner diameter of the stent 520′. Accordingly, the outer diameter of the first stent securement portion 582 may be greater than the inner diameter of the stent 520′ but less than the inner diameter of the stent 520″, and the outer diameter of the second stent securement portion 584 may be greater than the inner diameter of the stent 520″, as well as greater than the inner diameter of the stent 520′. It is recognized that the dimensions of the stent 520 and the stent securement portions 582, 584 may deviate from these examples, if desired.

Figure 14:
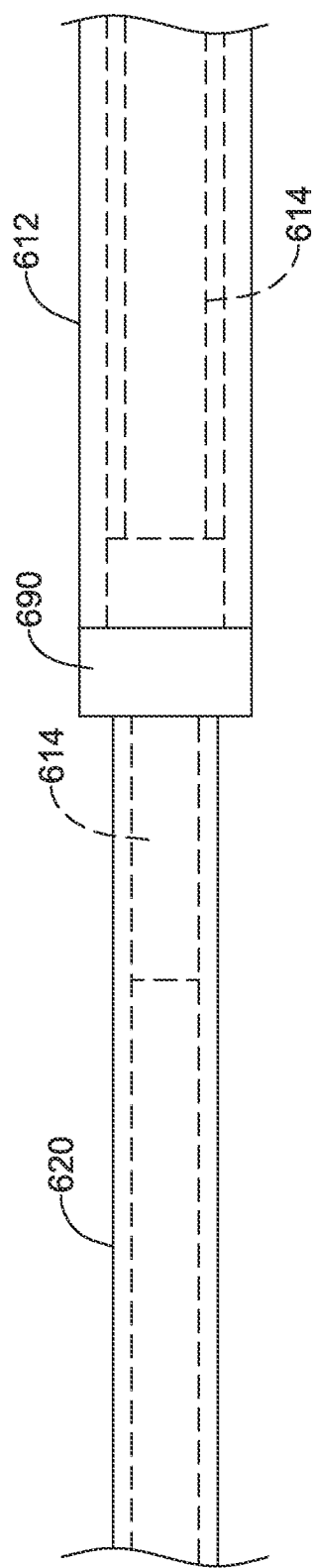
FIG. 14 is a plan view of features of an exemplary stent delivery system in accordance with this disclosure.

FIG. 14 illustrates features of an exemplary stent delivery system that may be incorporated into one of the stent delivery systems described above or another stent delivery system, if desired. The distal portion of an outer tubular member 612 and an associated inner member 614 of a stent delivery device, with an associated stent 620 is depicted.

In the embodiment of FIG. 14, the outer tubular member 612 may include a distal cap 690 positioned at a distal end thereof configured to abut the proximal end of the stent 620. The cap 690 may be formed of a different material than the remainder of the outer tubular member 612. For example, the cap 690 may be formed of a stiffer material, having a larger durometer than the remainder of the outer tubular member 612. In some instances, the cap 690 may be formed of a metallic material, while the remainder of the outer tubular member 612 may be formed of a polymeric material. In other instances, the cap 690 may be formed of a polymeric material having a larger durometer than the polymeric material forming the remainder of the outer tubular member 612. In some instances, the cap 690 may be radiopaque (e.g., formed of a radiopaque metallic material or be a polymer material doped with a radiopaque filler, etc.) such that the cap 690 is visible using fluoroscopic techniques. The increased stiffness of the cap 690 may facilitate engagement with the proximal end of the stent 620 as the outer tubular member 612 is longitudinally moved relative to the inner member 614 from the first position to the second position during deployment of the stent 620 from the stent delivery device.

In accordance with the embodiments described above, the distal end of the outer tubular member may be positioned proximal of the distal end of the inner member in the first position, and the distal end of the outer tubular member may be positioned distal of the distal end of the inner member in the second position to deploy a stent from the inner member. In moving from the first position to the section position, the outer tubular member may be moved distally relative to the inner member 14 about 5 to about 20 millimeters, about 5 millimeters to about 10 millimeters, about 10 millimeters to about 20 millimeters, about 5 millimeters, about 10 millimeters, about 15 millimeters, or about 20 millimeters, for example, to deploy the stent from the stent delivery device, for example. It is noted, however, that the stent delivery system may be configured to allow for a different amount of relative longitudinal movement to deploy the stent, if desired.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

Additional Examples

A first example includes a stent delivery device. The stent delivery device includes a handle assembly, an elongate inner member extending distally from the handle assembly along a longitudinal axis, and an elongate outer tubular member extending distally from the handle assembly along the longitudinal axis about the elongate inner member. The outer tubular member has a proximal end and a distal end, and the inner member has a proximal end and a distal end. The handle assembly includes a handle attached to one of the inner member and the outer tubular member, and an actuator attached to the other of the inner member and the outer tubular member. Actuation of the actuator relative to the handle between a first position and a second position causes axial movement of the outer tubular member relative to the inner member. The handle assembly also includes a locking mechanism for restricting actuation of the actuator from the first position to the second position. The locking mechanism has a locked position and an unlocked position. In the locked position the actuator is prevented from moving from the first position to the second position and in the unlocked position the actuator is permitted to move from the first position to the second position.

Additionally or alternatively, in a second example, the locking mechanism includes a protrusion on one of the handle and the actuator, the protrusion positioned in a channel formed in the other of the handle and the actuator.

Additionally or alternatively, in a third example, the actuator includes a knob positioned distal of a distal end of the handle, wherein knob moves distally relative to the distal end of the handle when the actuator is moved from the first position to the second position.

Additionally or alternatively, in a fourth example, the actuator includes an extension extending proximally from the knob into the handle, wherein the protrusion extends radially outward from the extension.

Additionally or alternatively, in a fifth example, the actuator is fixedly secured to the outer tubular member and the handle is fixedly secured to the inner member.

Additionally or alternatively, in a sixth example, the locking mechanism is rotatable about the longitudinal axis from the locked position to the unlocked position.

Additionally or alternatively, in a seventh example, the locking mechanism is movable independent of the actuator.

Additionally or alternatively, in an eighth example, in the locked position the locking mechanism obstructs a channel in the handle through which the actuator travels, and in the unlocked position the channel is unobstructed by the locking mechanism.

Additionally or alternatively, in a ninth example, the locking mechanism includes a threaded region of the actuator threadably engaged with a mating threaded region of the handle.

Additionally or alternatively, in a tenth example, the actuator is rotated relative to the handle about the longitudinal axis from the locked position to the unlocked position to disengage the threaded region of the actuator from the threaded region of the handle, wherein in the unlocked position the actuator is longitudinally movable relative to the handle to the second position.

Additionally or alternatively, in an eleventh example, the stent delivery device includes a stent surrounding a distal end region of the inner member in the first position.

Additionally or alternatively, in a twelfth example, the distal end of the outer tubular member is positioned proximal of the stent in the first position, and the distal end of the outer tubular member is positioned distal of the distal end of the inner member in the second position to deploy the stent from the inner member.

Additionally or alternatively, in a thirteenth example, the distal end of the outer tubular member is positioned proximal of the distal end of the inner member in the first position, and the distal end of the outer tubular member is positioned distal of the distal end of the inner member in the second position to deploy a stent from the inner member.

Another example is a method of manipulating a stent delivery device. The exemplary method includes grasping a handle of a handle assembly of the stent delivery device with a hand. The stent delivery device includes an elongate inner member extending distally from the handle assembly along a longitudinal axis, an elongate outer tubular member extending distally from the handle assembly along the longitudinal axis about the elongate inner member, and an actuator movable relative to the handle for providing longitudinal movement of the outer tubular member relative to the inner tubular member. The stent delivery device further includes a stent surrounding a distal end portion of the inner member. The method further includes moving a locking mechanism from a locked position to an unlocked position. In the locked position the locking mechanism prevents longitudinal movement of the outer tubular member relative to the inner tubular member and in the unlocked position longitudinal movement of the outer tubular member relative to the inner tubular member is permitted. Subsequently, the method includes actuating the actuator from a first position to a second position to deploy the stent from the stent delivery device. In the locked position the actuator is prevented from moving from the first position to the second position and in the unlocked position the actuator is permitted to move from the first position to the second position.

Additionally or alternatively, in an example, the locking mechanism is rotated about the longitudinal axis from the locked position to the unlocked position.

Additionally or alternatively, in an example, the steps of moving the locking mechanism from the locked position to the unlocked position and subsequently actuating the actuator from the first position to the second position to deploy the stent are performed with a single hand of an operator.

What is claimed is:

1. A stent delivery device, comprising:
a handle assembly;
an elongate inner member extending distally from the handle assembly along a longitudinal axis, the inner member having a proximal end and a distal end;
an elongate outer tubular member extending distally from the handle assembly along the longitudinal axis about the elongate inner member, the outer tubular member having a proximal end and a distal end;
the handle assembly including:
a handle attached to one of the inner member and the outer tubular member;
an actuator attached to the other of the inner member and the outer tubular member, wherein actuation of the actuator relative to the handle between a first position and a second position causes axial movement of the outer tubular member relative to the inner member; and
a locking mechanism for restricting actuation of the actuator from the first position to the second position, the locking mechanism having a locked position and an unlocked position;
wherein in the locked position the actuator is prevented from moving from the first position to the second position and in the unlocked position the actuator is permitted to move from the first position to the second position;
wherein the locking mechanism includes a protrusion on one of the handle and the actuator, the protrusion positioned in a channel formed in the other of the handle and the actuator;
wherein the channel includes a circumferential portion and a longitudinal portion, wherein the protrusion travels circumferentially in the circumferential portion of the channel when the locking mechanism is moved from the locked position to the unlocked position, and the protrusion travels longitudinally in the longitudinal portion of the channel when the actuator is moved to the second position.

2. The stent delivery device of claim 1, wherein the actuator includes a knob positioned distal of a distal end of the handle, wherein the knob moves distally relative to the distal end of the handle when the actuator is moved from the first position to the second position.

3. The stent delivery device of claim 2, wherein the actuator includes an extension extending proximally from the knob into the handle, wherein the protrusion extends radially outward from the extension.

4. The stent delivery device of claim 3, wherein the actuator is fixedly secured to the outer tubular member and the handle is fixedly secured to the inner member.

5. The stent delivery device of claim 1, wherein the locking mechanism is rotatable about the longitudinal axis from the locked position to the unlocked position.

6. The stent delivery device of claim 1, wherein the locking mechanism is movable independent of the actuator.

7. The stent delivery device of claim 6, wherein in the locked position the locking mechanism obstructs a channel in the handle through which the actuator travels, and in the unlocked position the channel is unobstructed by the locking mechanism.

8. The stent delivery device of claim 1, wherein the locking mechanism includes a threaded region of the actuator threadably engaged with a mating threaded region of the handle.

9. The stent delivery device of claim 8, wherein the actuator is rotated relative to the handle about the longitudinal axis from the locked position to the unlocked position to disengage the threaded region of the actuator from the threaded region of the handle, wherein in the unlocked position the actuator is longitudinally movable relative to the handle to the second position.

10. The stent delivery device of claim 1, further comprising a stent surrounding a distal end region of the inner member in the first position.

11. The stent delivery device of claim 10, wherein the distal end of the outer tubular member is positioned proximal of the stent in the first position, and the distal end of the outer tubular member is positioned distal of the distal end of the inner member in the second position to deploy the stent from the inner member.

12. A stent delivery assembly, comprising:
a handle assembly;
an elongate outer tubular member extending distally from the handle assembly along a longitudinal axis, the outer tubular member having a proximal end, a distal end, and a lumen extending therethrough;
an elongate inner member extending distally from the handle assembly through the lumen of the outer tubular member, the inner member having a proximal end and a distal end, the inner member including a distal portion extending distal of the distal end of the outer tubular member;
a tubular stent disposed about the distal portion of the inner member;
the handle assembly including:
a handle attached to one of the inner member and the outer tubular member;
an actuator attached to the other of the inner member and the outer tubular member, wherein actuation of the actuator relative to the handle from a first position to a second position causes axial movement of the outer tubular member relative to the inner member to deploy the stent from the distal portion of the inner member; and
a locking mechanism for restricting actuation of the actuator from the first position to the second position to prevent premature deployment of the stent, the locking mechanism having a locked position and an unlocked position;
wherein in the locked position the actuator is prevented from moving from the first position to the second position and in the unlocked position the actuator is permitted to move from the first position to the second position to deploy the stent;
wherein the locking mechanism includes a protrusion on one of the handle and the actuator, the protrusion positioned in a channel formed in the other of the handle and the actuator;
wherein the channel includes a circumferential portion and a longitudinal portion, wherein the protrusion travels circumferentially in the circumferential portion of the channel when the locking mechanism is moved from the locked position to the unlocked position, and the protrusion travels longitudinally in the longitudinal portion of the channel when the actuator is moved to the second position.

13. The stent delivery assembly of claim 12, wherein the actuator includes a knob positioned distal of a distal end of the handle and an extension extending proximally from the knob into the handle, wherein the knob moves distally relative to the distal end of the handle when the actuator is moved from the first position to the second position.

14. The stent delivery assembly of claim 13, wherein the extends radially outward from the extension.

15. A method of manipulating a stent delivery device, comprising:
grasping a handle of a handle assembly of the stent delivery device with a hand, the stent delivery device including:
an elongate inner member extending distally from the handle assembly along a longitudinal axis;
an elongate outer tubular member extending distally from the handle assembly along the longitudinal axis about the elongate inner member;
the handle attached to one of the inner member and the outer tubular member;
an actuator attached to the other of the inner member and outer tubular member and movable relative to the handle for providing longitudinal movement of the outer tubular member relative to the inner tubular member; and
a stent surrounding a distal end portion of the inner member;
moving a locking mechanism from a locked position to an unlocked position, wherein the locking mechanism includes a protrusion on one of the handle and the actuator, the protrusion positioned in a channel formed in the other of the handle and the actuator, wherein the channel includes a circumferential portion and a longitudinal portion, wherein in the locked position the locking mechanism prevents longitudinal movement of the protrusion within the channel and in the unlocked position the locking mechanism permits longitudinal movement of the protrusion within the channel; and
actuating the actuator from a first position to a second position to deploy the stent from the stent delivery device;
wherein in the locked position the protrusion is within the circumferential portion to prevent the actuator from moving from the first position to the second position and in the unlocked position the protrusion is not within the circumferential portion to permit the actuator to move from the first position to the second position.

16. The method of claim 15, wherein the locking mechanism is rotated about the longitudinal axis from the locked position to the unlocked position.

17. The method of claim 15, wherein the steps of: moving the locking mechanism from the locked position to the unlocked position and actuating the actuator from the first position to the second position to deploy the stent are performed with a single hand of an operator.

18. The method of claim 15, wherein the locking mechanism is movable from the locked position to the unlocked position independent of moving the actuator.

* * * * *